(12) United States Patent
Christensen et al.

(10) Patent No.: US 6,627,429 B1
(45) Date of Patent: Sep. 30, 2003

(54) PROCESS FOR ENZYMATICALLY MODIFYING PECTIN

(75) Inventors: Tove Martel Ida Else Christensen, Allerod (DK); Anette Amstrup Pedersen, Soborg (DK); Janne Brunstedt, Roskilde (DK); Jorn Dalgaard Mikkelsen, Hvidovre (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/787,069

(22) PCT Filed: Sep. 15, 1999

(86) PCT No.: PCT/IB99/01580
§ 371 (c)(1),
(2), (4) Date: Jul. 16, 2001

(87) PCT Pub. No.: WO00/15830
PCT Pub. Date: Mar. 23, 2000

(30) Foreign Application Priority Data

Sep. 16, 1998 (GB) .............................................. 9820195

(51) Int. Cl.[7] .............................. C12N 9/00; C12N 9/18; C12N 9/20; C12N 1/20; C12N 1/14; C12N 1/66; C12N 1/18; C07H 21/04
(52) U.S. Cl. ...................... 435/275; 435/41; 435/183; 435/197; 435/72; 435/101; 435/243; 435/252.1; 435/252.3; 435/254.1
(58) Field of Search ................................ 435/183, 197, 435/198, 72, 101, 275, 41, 243, 252.3, 254.1; 536/23.2, 23.7, 23.74

(56) References Cited

U.S. PATENT DOCUMENTS 4,200,694 A 4/1980 Ishii et al. .................. 435/101

FOREIGN PATENT DOCUMENTS

| WO | WO 97/03574 | * | 2/1997 | |
| WO | WO 97/31102 A | | 8/1997 | ............ C12N/9/18 |

OTHER PUBLICATIONS

Laurent et al. Gene, vol. 131:17–25, 1993.*
Plastow GS, Mol. Microbiol., vol. 2(2):247–254, 1988.*
PIR Database Accession No. JN0799, Laurent et al. May 3, 1994.*
PIR Database Accession No: S03770, Plastow et al. Jan. 12, 1989.*
Laurent et al., "Characterization and overexpression of the pem gene encoding pectin methylesterase of Erwinia chrysanthemi strain 3937", Gene, vol. 131, No. 1, 1993, pp. 17–25.
Plastow, G. S., "Molecular cloning and nucleotide sequence of the pectin methyl esterase gene of Erwinia chrysanthemi B374", Mol. Microbiol., vol. 2, No. 2, 1988, pp. 247–254.
Bordenave, "Analysis of Pectin Methyl Esterases", from "Modern Methods of Plant Analysis", vol. 17 (1996)(Linskens & Jackson Eds.), pp. 165–180.
Markovic and Kohn (1984) Experientia (Basel) 40:842–843.
Rexova–Benkova et al. (1976) Adv. Carbohydrate Chem. Biochem. 33:323–385.

* cited by examiner

*Primary Examiner*—Rebecca E. Prouty
*Assistant Examiner*—Manjunath N. Rao

(57) ABSTRACT

A process for treating a pectin with a pectin methyl esterase (PME) is descibed. Here, the PME is not a plant PME—but the PME is capable of exhibiting at least one plant PME property; wherein the at least one plant PME property comprises at least block—wise de-esterification of the pectin.

34 Claims, 3 Drawing Sheets

PROCESS FOR ENZYMATICALLY MODIFYING PECTIN

Figure 1:
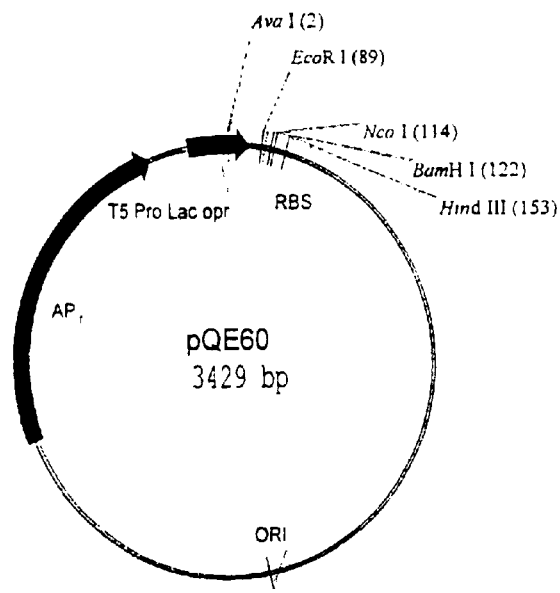

The present invention relates to a process.

In particular, the present invention relates to a process which comprises the use of an enzyme.

More in particular, the present invention relates to a process for enzymatically modifying pectin.

Pectin is a structural polysaccharide commonly found in the form of protopectin in plant cell walls. The backbone of pectin comprises linked (1→4)-α-D-galacturonic acid residues which are interrupted with a small number of 1→2 linked α-L-rhamnose units.

In addition, pectin comprises highly branched regions with an almost alternating rhatnno-galacturonan chain. These highly branched regions also contain other sugar units (such as D-galactose, L-arabinose and xylose) attached by glycosidic linkages to the C3 or C4 atoms of the rhamnose units or the C2 or C3 atoms of the galacturonic acid units. . The long chains of -(1→4)-αlinked galacturonic acid residues are commonly referred to as "smooth" regions, whereas the highly branched regions are commonly referred to as the "hairy regions".

Some of the carboxyl groups of the galacturonic residues are esterified (e.g. the carboxyl groups are metbylated). By way of example some galacturonic acid residues are esterified with methanol. Typically esterification of the carboxyl groups occurs after polymerisation of the galacturonic acid residues. However, it is extremely rare for all of the carboxyl groups to be esterified (e.g. methylated).

Usually, the degree of esterification will vary from 0–90%. If 50% or more of the carboxyl groups are esterified then the resultant pectin is referred to as a "high ester pectin" ("HE pectin" for short) or a "high methoxyl pectin". If less than 50% of the carboxyl groups are esterified then the resultant pectin is referred to as a "low ester pectin" ("LE pectin" for short) or a "low methoxyl pectin". If 50% of the carboxyl groups are esterified then the resultant pectin is referred to as a "medium ester pectin" ("ME pectin" for short) or a "medium methoxyl pectin". If the pectin does not contain any—or only a few—esterified groups it is usually referred to as pectic acid.

The structure of the pectin, in particular the degree of esterification (e.g. methylation), dictates many of the resultant physical and/or chemical properties of the pectin. For example, pectin gelation depends.on the chemical structure of the pectin, especially the degree of esterification. In addition, however, pectin gelation also depends on the soluble-solids content, the pH and calcium ion concentration. With respect to the latter, it is known that the calcium ions form complexes with free carboxyl groups, particularly those on a LE pectin.

Pectic enzymes are classified according to their mode of attack on the galacturonan part of the pectin molecule. A review of some pectic enzymes has been prepared by Pilnik and Voragen (Food Enzymology, Ed.: P. F. Fox; Elsevier; (1991); pp: 303–337). In particular, pectin methylesterases (EC 3.1.1.11), otherwise referred to as PMEs, de-esterify HE pectins to LE pectins or pectic acids. In contrast, and by way of example, pectin depolymerases split the glycosidic linkages between galacturonosyl methylester residues.

In more detail, PME activity produces free carboxyl groups and free methanol. The increase in free carboxyl groups can be easily monitored by automatic titration. In this regard, earlier studies have shown that some PMEs de-esterify pectins in a random manner, in the sense that they de-esterify any of the esterified (e.g. methylated) galacturonic acid residues on one or more than one of the pectin chains. Examples of PMEs that randomly de-esterify pectins may be obtained from fungal sources such as *Aspergillus aculeatus* (see WO 94/25575) and *Aspergillus japonicus* (Ishii et al 1980 J Food Sci 44 pp 611–14). Baron et al (1980 Lebensm. Wiss. μ-Technol. 13pp 330–333) apparently have isolated a fungal PME from *Aspergillus niger*. This fungal PME is reported to have a molecular weight of 39000 D, an isoelectric point of 3.9, an optimum pH of 4.5 and a $K_m$ value (mg/ml) of 3.

In contrast, some PMEs are known to de-esterify pectins in a block-wise manner, in the sense that it is believed they attack pectins either at non-reducing ends or next to free carboxyl groups and then proceed along the pectin molecules by a single-chain mechanism, thereby creating blocks of un-esterified galacturonic acid units which can be calcium sensitive. Examples of such enzymes that block-wise enzymatically de-esterify pectin are plant PMEs. Up to 12 isoforms of PME have been suggested to exist in citrus (Pilnik W. and Voragen A. G. J. (Food Enzymology (Ed.: P. F. Fox); Elsevier; (1991); pp: 303–337). These isoforms have different properties.

Random or blockwise distribution of free carboxyl groups can be distinguished by high performance ion exchange chromatography (Schols et al Food Hydrocolloids 1989 6 pp 115–121). These tests are often used to check for undesirable, residual PME activity, in citrus juices after pasteurisation because residual PME can cause, what is called, "cloud loss" in orange juice in addition to a build up of methanol in the juice.

PME substrates, such as pectins obtained from natural plant sources, are generally in the form of a high ester pectin having a DE of about 70%. Sugar must be added to extracts containing these high ester PME substrates to provide sufficient soluble solids to induce gelling. Usually a minimum of 55% soluble solids is required.

Syneresis may occur. By way of example, syneresis in marmalades and jams with low soluble solid content (<55%) may occur when using HE-pectin. However, HE-pectin is not usually used in such applications. If pectins are to be used, then typically amidated pectins or LE-pectin are used, such as for jams with <55% SS.

When syneresis does occur, expensive additives must be used to induce gelline.

Versteeg et al (J Food Sci 45 (1980) pp 969–971) apparently have isolated a PME from orange. This plant PME is reported to occur in multiple isoforms of differing properties. Isoform I has a molecular weight of 36000 D, an isoelectric point of 10.0, an optimum pH of 7.6 and a $K_m$ value (mg/ml) of 0.083. Isoform II has a molecular weight of 36200 D. an isoelectric point of 11.0, an optimum pH of 8.8 and a $K_m$ value (mg/ml) of 0.0046. Isoform III (HMW-PE) has a molecular weight of 54000 D, an isoelectric point of 10.2, an optimum pH of 8 and a $k_m$ value (mg/ml) of 0.041. However, to date there has been very limited sequence data for such PMEs.

According to Pilnik and Voragen (ibid), PMEs may be found in a number of other higher plants, such as apple, apricot, avocado, banana, berries, lime, grapefruit, mandarin, cherries, currants, grapes, mango, papaya, passion fruit, peach, pear, plums, beans, carrots, cauliflower, cucumber, leek, onions, pea, potato, radish and tomato. However, likewise, so far there has been very limited sequence data for such PMEs.

A plant PME has been reported in WO-A-97/03574 (the contents of which are incorporated herein by reference). This PME has the following characteristics: a molecular weight of from about 36 kD to about 64 kD; a pH optimum of pH 7–8 when measured with 0.5% lime pectin in 0.15 M NaCl; a temperature optimum of at least 50° C.; a temperature stability in the range of from 10°—at least 40° C.; a $k_m$ value of 0.07%; an activity maximum at levels of about 0.25 M NaCl; an activity maximum at levels of about 0.2 M $Na_2SO_4$; and an activity maximum at levels of about 0.3 M $NaNO_3$.

Another PME has been reported in WO 97/31102 (the contents of which are incorporated herein by reference).

PMEs have important uses in industry. For example, they can be used in or as sequestering agents for calcium ions. In this regard, and according to Pilnik and Voragen (ibid), cattle feed can be prepared by adding a slurry of calcium hydroxide to citrus peels after juice extraction. After the addition, the high pH and the calcium ions activate any native PME in the peel causing rapid de-esterification of the pectin and calcium pectate coagulation occurs. Bound liquid phase is released and is easily pressed out so that only a fraction of the original water content needs to be removed by expensive thermal drying. The press liquor is then used as animal feed.

As indicated above, a PME has been obtained from *Aspergillus aculeatus* (WO 94/25575). Apparently, this PME can be used to improve the firmness of a pectin-containing material, or to de-methylate pectin, or to increase the viscosity of a pectin-containing material.

It has also become common to use PME in the preparation of foodstuffs prepared from fruit or vegetable materials containing pectin—such as jams or preservatives. For example, WO-A-94/25575 further reports on the preparation of orange marmalade and tomato paste using PME obtained from *Aspergillus aculeatus*.

JP-A-63/209553 discloses gels which are obtained by the action of pectin methylesterase, in the presence of a polyvalent metal ion, on a pectic polysaccharide containing as the main component a high-methoxyl poly α-1,4-D-galacturonide chain and a process for their production.

Pilnik and Voragen (ibid) list uses of endogenous PMEs which include their addition to fruit juices to reduce the viscosity of the juice if it contains too much pectin derived from the fruit, their addition as pectinase solutions to the gas bubbles in the albedo of citrus fruit that has been heated to a core temperature of 20° C. to 40° C. in order to facilitate removal of peel and other membrane from intact juice segments (U.S. Pat. No. 4,284,651), and their use in protecting and improving the texture and firmness of several processed fruits and vegetables such as apple (Wiley & Lee 1970 Food Technol 24 1168–70) canned tomatoes (Hsu et al 1965 J Food Sci 30 pp 583–588) and potatoes (Bartolome & Hoff 1972 J Agric Food Chem 20 pp 262–266).

Glahn and Rolin (1994 Food Ingredients Europe, Conf Proceedings pp 252–256) report on the hypothetical application of the industrial "GENU pectin type YM-100" for interacting with sour milk beverages. No details are presented at all on how GENU pectin type YM-100 is prepared.

EP-A-0664300 discloses a chemical fractionation method for preparing calcium sensitive pectin. This calcium sensitive pectin is said to be advantageous for the food industry.

Plastow G. S. (1988 Molecular Microbiology 2(2) 247–254) reports on a pectin methyl esterase gene of *Erwinia chrysanthemi* B374. According to the author:

"The isolation of the Erwinia gene provides a simple method for the production of PME free from depolymerizing pectinases thereby extending its potential uses".

Plastow G. S. further states that:

"The PME . . . produced from *E.coli* supernatants has been used successfully to de-esterify high-methoxyl pectin for the production of calcium-set gels. The gels that were obtained were found to equal those made from pectate produced using enzyme extracted from orange peel ( . . . unpublished results)."

Thus, pectins and de-esterified pectins, in addition to PMEs, have an industrial importance.

However, and as reported in PCT/IB98/00673 (filed Apr. 24, 1998), a benefit derived from use of a PME in the preparation of, for example, a foodstuff will depend to some extent on the quality and quantity and type of the PME used and on the qualiy and quantity and type of the PME substrates—in particular pectin—that may be present in the material used to prepare the foodstuff. For example, if the substrate is a fruit material or a vegetable material then the amount and/or structure of natural pectin in that substrate will be different for different types of fruit material or vegetable material. This is also borne out by the data presented in WO-A-94/25575, especially FIG. 7 where it is clear to see that its PME system is not ideal.

According to a first aspect of the present invention there is provided a process for treating a pectin with a pectin methyl esterase (PME); wherein the PME is not a plant PME; but wherein the PME is capable of exhibiting at least one plant PME property; and wherein the at least one plant PME property comprises at least block-wise de-esterification of the pectin.

According to a second aspect of the present invention there is provided a PME treated pectin prepared by the process according to the present invention.

According to a third aspect of the present invention there is provided a foodstuff comprising a PME treated pectin prepared by the process according to the present invention.

According to a fourth aspect of the present invention there is provided use of a PME as herein defined to reduce the number of ester groups in a pectin and in a block-wise manner.

According to a fifth aspect of the present invention there is provided the use of a PME as herein defined to de-esterify two or more adjacent galacturonic acid residues of a pectin on at least substantially all of the pectin chains.

The present invention also relates to any one or more of:

a construct expressing or comprising the PME as defined herein or the nucleotide sequence as defined herein.

a vector expressing or comprising a construct of the present invention or the PME as defined herein or the nucleotide sequence as defined herein.

a combination of constructs comprising at least a first construct expressing or comprising the PME enzyme as defined herein or the nucleotide sequence as defined herein; and a second construct comprising a gene of interest (GOI) and a promoter.

a cell, tissue or organ expressing or comprising a vector according to the present invention or a construct according to the present invention or the PME as defined herein or the nucleotide sequence as defined herein or the combination of constructs according to the present invention.

a transgenic organism expressing or comprising a cell, tissue or organ expressing or comprising a vector according to the present invention or a construct according to the present invention or the PME as defined herein or the nucleotide sequence as defined herein or the combination of constructs according to the present invention.

a recombinant PME enzyme which is immunologically reactive with an antibody raised against a PME enzyme as defined herein.

In addition to the sequences presented in the attached sequence listings (as well as fragments, derivatives or homologues thereof), the present invention also covers sequences that are complementary to the aforementioned sequence listings (as well as fragments, derivatives or homologues thereof). The present invention also covers sequences that can hybridise to the aforementioned sequence listings (as well as fragments, derivatives or homologues thereof). The present invention also covers sequences that are complementary to sequences that can hybridise to the aforementioned sequence listings (as well as fragments, derivatives or homologues thereof).

The present invention also relates to novel amino acid sequences and novel nucleotide sequences presented herein.

Preferably, those novel amino acid sequences and novel nucleotide sequences are isolated and/or purified. Here the term "isolated" and "purified" refer to molecules, either nucleic or amino acid sequences, that are removed from their natural environment and isolated or separated from at least one other component with which they are naturally associated.

The present invention is based on the highly surprising finding that it is possible to obtain PMEs from sources other than plants that are capable of block-wise de-esterifying pectins but wherein those PMEs have plant PME like properties.

More in particular, the present invention is based on the highly surprising finding that it is possible to obtain PMEs from bacterial sources that are capable of block-wise de-esterifying pectins.

The present invention is distinguishable over the teachings of, for example, Plastow G. S. (ibid) as that author does not disclose block-wise de-esterification of pectins. Moreover, that author refers to unpublished work that includes a comparison with an "enzyme extracted from orange peel"—and yet no details are provided on what enzyme, let alone enzymatic activity, is used in the comparative studies. Moreover, the reference to "calcium set" gels and the comparison to pectate produced gels in that paper indicate that the pectins were de-esterified to low ester pectins—which is in direct contrast to a highly preferred aspect of the present invention.

Thus, the present invention relates to a process for treating a pectin with a PME; wherein the PME is not a plant PME; but wherein the PME is capable of exhibiting at least one plant PME property; and wherein the at least one plant PME property comprises at least block-wise de-esterification of the pectin.

Preferably, the PME has a molecular weight of about 36.000 D and/or a pI of about >9 and/or a pH optimum with lime pectin (as determined by the aforementioned method) of about pH 7 and/or a temperature optimum with lime pectin (as determined by the aforementioned method) of about 48° C.

Preferably, the PME comprises the amino acid sequence shown as SEQ.I.D. No.2 or a variant, derivative or homologue thereof, including combinations thereof.

Preferably, the PME has the amino acid sequence shown as SEQ.I.D. No.2, or a variant, derivative or homologue thereof.

Preferably, the PME has the amino acid sequence shown as SEQ.I.D. No.2.

Preferably, the PME has been expressed by a nucleotide sequence comprising the nucleotide sequence shown as SEQ.I.D. No. 1, or a variant, derivative or homologue thereof, or combinations thereof.

Preferably, the PME has been expressed by a nucleotide sequence having the nucleotide sequence shown as SEQ.I.D. No. 1 or a variant, derivative or homologue thereof.

Preferably, the PME has been expressed by a nucleotide sequence having the nucleotide sequence shown as SEQ.I.D. No. 1.

Preferably, the PME has been prepared by use of recombinant DNA techniques.

Preferably, the PME is obtainable from a micro-organism, preferably a bacterium.

Preferably, the pectin is treated by the PME in the presence of sodium ions.

Preferably, the sodium ions are derived from NaCl, $NaNO_3$ or $Na_2SO_4$ or combinations thereof.

Preferably, the process includes the further step of isolating the PME treated pectin from the active PME. Here, the PME treated pectin can be physically removed from the active PME or vice versa. Preferably, however, the PME treated pectin is isolated from the active PME by simply inactivating the PME, such as through the application of heat.

Preferably, the PME treated pectin is a high ester pectin.

Preferably, the PME treated pectin contains from about 70% to about 80% ester groups.

Preferably, the PME treated pectin contains from about 72% to about 80% ester groups.

Preferably, the PME treated pectin contains from about 74% to about 80% ester groups.

Preferably, the PME treated pectin contains from about 76% to about 80% ester groups.

Preferably, the PME treated pectin contains from about 77% to about 79% ester groups.

Preferably, the PME treated pectin contains about 78% ester groups.

Preferably, the process includes the further step of adding the PME treated pectin to a medium that is suitable for consumption.

Preferably, the medium is an aqueous solution.

Preferably, the medium is an acidic environment.

Preferably, the acidic environment has a pH of from about 3.5 to about 5.5, preferably wherein the acidic environment has a pH of from 4 to about 5.5.

Preferably, the acidic environment has a pH of about 4.

Preferably, the aqueous solution is a beverage.

Preferably, the beverage is an acidified milk drink, drinking yoghurt, a milk drink comprising fruit, or a beverage enriched with proteins, such as plant and/or dairy proteins, such as whey protein and/or soya protein. A protocol for determining the suitability of a treated pectin for use in a drink is shown after the Examples Section.

Acidified milk drinks with loner shelf life are very popular, especially in the Far East. In some cases, a heat treatment is necessary to obtain a long shelf life. In order to avoid sedimentation of protein during and after heating, pectin is added as a stabilising agent. In some applications, the quality of the acidified milk drink may depend on the properties and the concentration of the pectin used.

In one preferred aspect, the medium comprises and/or is enriched with a protein. Here, preferably, the protein is either derived from or is derivable from or is in a dairy product, such as milk or cheese—preferably wherein the protein is casing or whey protein—and/or derived from or is derivable from or is in a plant product.

If the beverage is an acidified milk drink, then it is typically prepared by acidifying the milk and then adding the pectin at a low pH.

If the beverage is a soya protein drink, then it is typically prepared by solubilising the soya protein at neutral pH. The pectin is added by solubilization in the soya protein solution at neutral pH. Then, the solution is acidified by addition e.g. fruit juice.

The use of a block-wise enzymatically de-esterified pectin—which is preferably prepared by use of recombinant DNA techniques—is of benefit as it allows proteins such as whey and milk proteins (such as casein) to be stable in acidic solutions. This is of importance for the drinks market, such as skimmed milk, fruit juices and whey protein drinks, wherein before it was only possible to retain the flavour of the key proteins under fairly high acidic conditions—such as pH 4.2—if high amounts of stabiliser were present.

We have now found that for some applications small amounts of the de-esterified pectin prepared by the process of the present invention can be employed. At these low levels, the de-esterified pectin according to the present invention not only acts as a stabiliser but also it does not have an adverse effect on the final product.

If desired, the use of the de-esterified pectin of the present invention would enable food manufacturers to increase the pH of foods, such as drinks. In this regard, in some cases the less acidic nature of the drinks may make them more palatable for people, especially infants. Thus, in contrast to the prior art processes, it is now possible to retain the flavour of those proteins at pH conditions higher than 4.2, such as up to pH 5.5 (such as pH 5.2) by use of the block-wise enzymatically de-esterified pectin, particularly the block-wise enzymatically de-esterified pectin prepared by use of, for example, recombinant DNA techniques.

In addition, it is believed that even under low pH conditions, such as pH 4.2 or less, the block-wise enzymatically de-esterified pectin—particularly the block-wise enzymatically de-esterified pectin (preferably prepared by use of recombinant DNA techniques)—stabilises the protein(s) more than the prior art stabilisers that are used for those pH conditions.

A further advantage is that the PME of the present invention is capable of producing a substantially homogeneous block-wise de-esterified pectin. By this we mean that substantially all of the pectin chains comprise at least two adjacent de-esterified carboxyl groups. However, for some applications it may not be necessary to prepare or use such a substantially homogeneous block-wise de-esterified pectin.

Without wishing to be bound by theory it is believed that the block-wise enzymatically de-esterified pectin— particularly that prepared by use of recombinant DNA techniques—stabilises the protein(s) by surrounding the protein(s) in a blanket of negative charges, thus forming a stable entity.

The PME enzyme of the present invention is useful for blockwise de-esterifying pectins when the pectins are contacted with the enzyme in a substantially aqueous medium. In some instances, de-esterifying pectins can increase the calcium ion sensitivity of a pectin—which in turn may be advantageous.

Alternatively, the PME enzyme of the present invention is useful for esterifying pectins when the pectins are contacted with the enzyme in a substantially non-aqueous medium, such as in the presence of methanol or in the presence of high concentrations of ammonium sulphate. This aspect is advantageous if, for example, it is desirable to reduce the calcium sensitivity of a pectin.

This method of esterifying pectins is advantageous because it obviates the need for the high temperature and methanol esterification conditions associated with the prior art processes. Thus, the present invention also includes the use of that esterified pectin in the preparation of a foodstuff as well as the pectin per se.

In accordance with the present invention, the de-esterified pectin of the present invention is advantageous for the preparation of a foodstuff.

Preferably, the foodstuff is food for human and/or animal consumption. Typical preferred foodstuffs include jams, marmalades, jellies, dairy products (such as milk or cheese), meat products, poultry products, fish products and bakery products. The foodstuff may even be a beverage. The beverage can be a drinking yoghurt, a fruit juice or a beverage comprising whey protein.

In addition to the foodstuff comprising the PME treated pectin, the foodstuff may comprise more other components, such as one or more suitable food ingredients. Typical food ingredients include any one or more of an acid—such as citric acid—or a sugar—such as sucrose, glucose or invert sugar—or fruit—or other enzymes, preservatives, colourings and other suitable components.

In one preferred embodiment, the foodstuff of the present invention comprises fruit. Here, fruit imparts taste, colour and structure to the gel, as well as pectin, acid and a small amount of solids. Depending on the level of natural flavour and colour in the fruit, fruit dosages are normally from 25% to 60% of the jam. The solids content of ordinary fruit is around 10% Brix, but fruit concentrate, which is typically 65–70% Brix, can also be used. The pH in fruit varies widely, depending on the fruit in question, but most fruits have a pH between 3.0 and 3.5.

The pectin content also varies, depending on the fruit in question. For example, redcurrants, blackcurrants and oranges have a high pectin content, and satisfactory gels from these fruits can be obtained by adding only a small amount of extra pectin. The choice of pectin depends on the type of jam in question. For example, GRINDSTED™ Pectin SS 200 is used in jams containing no fruit pieces or jam containing only very small fruit pieces. Fruit separation in such jams is not a problem, and consequently a slow-setting pectin and lower filling temperature can be used.

By way of example, GRINDSTED™ Pectin RS 400 is used in jams containing large fruit pieces or whole fruit, for instance cherries or strawberries. In jams containing whole fruit it may be difficult to avoid fruit separation, and it is therefore necessary to use a rapid-set pectin such as GRINDSTED™ Pectin RS 400.

The choice of pectin type may also depend on the container size in question. When standard jars are used, the filling temperature is less critical with regard to the stability of pectin, as the jars will cool down relatively quickly after filling and the pectin sill not degrade. However, if the jam is filled into large containers, eg 500 or 1,000 kg, the cooling time will be very long. In the centre of such a large container the pectin will be especially subject to degradation, and the gel will be weaker at the centre than at the sides. Consequently, a more slow-setting pectin is generally used for large containers, allowing filling at lower temperatures and thereby avoiding degradation of the pectin.

Sugar is added to jam for various reasons, such as:
1. To provide soluble solids—HE pectins can require a minimum soluble solids content of 55% before they will gel
2. To provide sweetness
3. To provide increased physical, chemical and microbiological stability
4. To provide an improved mouthfeel
5. To provide improved colour and gloss Sucrose is the sugar normally used, but other sugars may well be used depending on the taste, sweetening effect, crystallisation or structure required. Price may also influence which type of sugar is used.

Invert sugar has the same sweetening effect as sucrose, whereas glucose syrup, glucose and sorbitol have a reduced sweetening effect. High fructose corn syrup and fructose will have a greater sweetening effect than sucrose.

The structure and strength of the gel as well as the gelling temperature will, to some extent, be influenced by changes in sugar composition.

Acid is added for two reasons: 1) partly to reduce the pH level to 3.0–3.2 to obtain a satisfactory gel with the pectin, and 2) partly to enhance the flavour of the fruit. The optimum pH for gelation using the HE pectins depends on the type of pectin and solids content in question.

If GRINDSTED™ Pectin SS 200 is used in jam with 65–68% Brix, the optimum pH is 3.0–3.2. If the solids content is higher than this, the optimum pH is 3.1–3.3. Conversely, if the solids content is lower the optimum pH is 2.8–3.0. If GRINDSTED™ Pectin RS 400 is used, the optimum pH is approximately 0.2 units higher than for GRINDSTED™ Pectin SS 200.

The acid most commonly used is citric acid, monohydrate, in a 50% w/v solution.

Other acids (such as malic acid, tartaric acid or phosphoric acid) may be used but must always be in solution.

The choice of acid depends on legislation, price, and the tartness of sweetness required in the finished product.

Citric acid imparts a relatively strong acid taste to the finished product, whereas malic acid results in a softer but longer-lasting taste.

Tartaric acid may result in a slightly bitter taste, and phosphoric acid results in a sweeter taste.

Enzymaticallly treated pectin can prevent syneresis which can often occur in the manufacture of marmalades and jams with low soluble solids contents.

In some instances, the de-esterified pectin of the present invention is also advantageous for use as a stabiliser and/or viscosity modifier in the preparation of pharmaceuticals, pharmaceutical appliances, cosmetics and cosmetic appliances.

Preferably the block-wise enzymatically de-esterified pectin is a high ester pectin containing about 80% ester groups or less (i.e. a degree of esterification (DE) of 80% or less), preferably about 75% ester groups or less (i.e. a DE of about 75% or less). In this regard, the ratio of free carboxyl groups to esterified carboxyl groups on the pectin is from 1:1 to 1:4, preferably from 1:2 to 1:3.

Preferably, the block-wise enzymatically de-esterified pectin contains about 78% ester groups.

A Protocol for determining the degree of esterification of the PME substrate may be found on page 58 of WO-A-97/03574 (the contents of which are incorporated herein by reference). For ease of reference, this Protocol is recited after the Examples Section A Protocol for determining calcium sensitivity may be found on page 57 of WO-A-97/03574 (the contents of which are incorporated herein by reference). For ease of reference, this Protocol is also recited after the Examples Section.

Preferably the block-wise enzymatically de-esterified pectin has a high molecular weight. Typically, the molecular weight is between from about 50 KD to about 150 KD.

Preferably the block-wise enzymatically de-esterified pectin is prepared by treating a pectin with a PME that de-esterifies two or more adjacent galacturonic acid residues of the pectin on at least substantially all of the pectin chains.

Preferably the PME is derived from a PME obtainable from a micro-organism, preferably a bacterium.

The term "derived from a PME obtainable from a micro-organism" means that the PME has a sequence similar to that of a PME that is obtainable from a micro-organism providing the PME can de-esterify pectin in a block-wise manne The term "derived from a PME obtainable from a bacterium" means that the PME has a sequence similar to that of a PME that is obtainable from a bacterium, providing the PME can de-esterify pectin in a block-wise manner.

The term "pectin" includes pectin in its normal sense, as well as fractions and derivatives thereof, as well as modified pectins (e.g. chemically modified pectins and enzymatically modified pectins).

By way of example the pectin can be a derivatised pectin, a degraded (such as partially degraded) pectin or a modified pectin. An example of a modified pectin is pectin that has been prior treated with an enzyme such as a PME—which may be the same as the PME of the present invention or a different PME or a combination thereof. An example of a pectin derivative is pectin that has been chemically treated— eg. amidated.

Preferably, the pectin is not a pectin that has been prior treated with the enzyme polygalacturonase to substantially reduce the length of the pectin backbone.

As indicated, in a preferred aspect, the present invention encompasses variants, homologues and derivatives of the sequences presented herein. The present invention also encompasses fragments of such sequences.

The terms "variant", "homologue" or "fragment" in relation to the recombinant enzyme of the present invention include any substitution of, variation of, modification of, replacement of, deletion of or addition of one (or more) amino acid from or to the sequence providing the resultant amino acid sequence has PME activity, preferably having at least the same activity of a recombinant enzyme comprising sequence shown as SEQ I.D. No. 2. In particular, the term "homologue" covers homology with respect to structure and/or function providing the resultant recombinant enzyme has PME activity. With respect to sequence homology (i.e. similarity), preferably there is at least 75%, more preferably at least 85%, more preferably at least 90% homology to the sequence shown in the attached sequence listings. More preferably there is at least 95%, more preferably at least 98%, homology to the sequence shown in the attached sequence listings.

Thus, enzymes of the present invention may also be modified to contain one or more (e.g. at least 2, 3, 5, or 10) substitutions, deletions or insertions, including conserved substitutions.

By way of example, conservative substitutions may be made, for example according to the Table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

As indicated above, proteins of the invention are typically made by recombinant means for example as described herein and/or by using synthentic means techniques well known to skilled persons such as solid phase synthesis. Variants and derivatives of such sequences include fusion proteins, wherein the fusion proteins comprise at least the amino acid sequence of the present invention being linked (directly or indirectly) to another amino acid sequence. These other amino acid sequences—which are sometimes referred to as fusion protein partners—will typically impart a favourable functionality—such as to aid extraction and purification of the amino acid sequence of the present invention. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of the present invention so as to allow removal of the latter. Preferably the fusion protein partner will not hinder the function of the protein of the present invention.

In one aspect, the variant, homologue, derivative, or fragment of the amino acid sequence according to the present invention may comprise at least the following domain—which we have presented as Formula (I):

A1-A2-A3-A4-A5-A6-A7-A8-A9-A10-A11-A12-A13-A14-A15-A16-A17-A18-A19-A20-A21-A22  (I)

wherein

A1 is a hydrophobic or polar amino acid or a neutral amino acid

A2 is a hydrophobic amino acid

A3 is a hydrophobic amino acid

A4 is a polar amino acid

A5 is a polar or charged amino acid or neutral amino acid

A6 is a polar amino acid

A7 is a polar or charged or hydrophobic amino acid

A8 is a hydrophobic amino acid

A9 is a hydrophobic or polar amino acid

A10 is a hydrophobic or polar amino acid

A11 is a charged amino acid

A12 is a charged or polar or hydrophobic amino acid

A13 is a hydrophobic or charged amino acid or neutral amino acid

A14 is a hydrophobic or polar amino acid or charged or neutral amino acid

A15 is a charged or polar or hydrophobic amino acid

A16 is a polar or hydrophobic or charged amino acid or neutral amino acid

A17 is a polar or charged amino acid or neutral amino acid

A18 is a polar or charged or hydrophobic amino acid

A19 is a polar amino acid or a neutral amino acid

A20 is a hydrophobic or polar amino acid

A21 is a hydrophobic amino acid

A22 is a polar or hydrophobic amino acid.

This domain is described in our earlier UK patent application No. 9910935.7 filed May 11, 1999.

In this aspect of the present invention, preferably, A1 is a hydrophobic amino acid.

Preferably A5 is a polar amino acid.
Preferably A7 is a polar amino acid.
Preferably A9 is a hydrophobic amino acid.
Preferably A10 is a hydrophobic amino acid.
Preferably A12 is a charged amino acid.
Preferably A13 is a hydrophobic amino acid.
Preferably A14 is a hydrophobic amino acid.
Preferably A15 is a charged amino acid.
Preferably A16 is a polar amino acid.
Preferably A17 is a polar amino acid.
Preferably A18 is a polar amino acid.
Preferably A20 is a hydrophobic amino acid.
Preferably A22 is a polar amino acid.

For the amino acid sequence of formula (I), preferable examples of hydrophobic amino acids may include: Ala (A), Val (V), Phe (F), Pro (P), Met (M), Ile (I), Leu (L).

For the amino acid sequence of formula (I), preferable examples of charged amino acids may include Asp (D), Glu (E), Lys (K), Arg (R).

For the amino acid sequence of formula (I), preferable examples of polar amino acids may include: Ser (S), Thr (T), Tyr (Y), His (H), Cys (C), Asn (N), Gln (Q), Trp (W).

For the amino acid sequence of formula (I), a preferable example of a neutral amino acid is glycine (G).

Preferably A1 is A, V, G or T.
Preferably A2 is V or L.
Preferably A3 is L, F or I.
Preferably A4 is Q.
Preferably A5 is N, D, K, G or S.
Preferably A6 is C or S.
Preferably A7 is D, Q, K, E, Y or L.
Preferably A8 is I, L or F.
Preferably A9 is H, N, V, M or L.
Preferably A10 is A, C, I, P, L, C or S.
Preferably A11 is R.
Preferably A12 is K, R, L, Q or Y.
Preferably A13 is P, G or R.
Preferably A14 is N, G, M, A, L, R or S.
Preferably Al5 is S, K, E, P or D.
Preferably A16 G, Y, H, N, K or V.
Preferably A17 is Q, G or K.
Preferably A18 is K, Q, F, Y, T or S.
Preferably A19 is N, C or G.
Preferably A20 is M, L, I, T, V, H or N.
Preferably A21 is V or I.
Preferably A22 is T, L or S.

We also believe that the amino acid sequence should retain the amino acid of sequence presented as formula (II):

N-N-N-N-N-N-N-N-N-N-N-N-N-N-H-H-N-H-N-N-N-N-N-N-
N-N-N-N-N-N-H-N-N-N-P-C-P-H-N-H-N-N-N-N-N-N-N-N-
N-N-N-N-N-N-N-N-N-N-N-N-N-N-H-N-G-N-N-C-N-H-H-G-
N-N-N  (II)

wherein

H independently represents a hydrophobic amino acid

C independently represents a charged amino acid

P independently represents a polar amino acid

G represents glycine

N independently represents glycine or a hydrophobic or charged or polar amino acid.

For the amino acid sequence of formula (II): examples of hydrophobic amino acids include: Ala (A), Val (V), Phe (F), Pro (P), Met (M), lie (I), Leu (L); examples of charged amino acids include Asp (D), Glu (E), Lys (K), Arg (R); and examples of polar amino acids include: Ser (S), Thr (T), Tyr (Y), His (H), Cys (C), Asn (N), Gln (Q), Trp (W).

The terms "variant", "homologue" or "fragment" in relation to the nucleotide sequence coding for the recombinant enzyme of the present invention include any substitution of, variation of, modification of, replacement of, deletion of or addition of one (or more) nucleic acid from or to the sequence providing the resultant nucleotide sequence codes for a recombinant enzyme having PME activity, preferably having at least the same activity of a recombinant enzyme comprising the sequence shown as SEQ I.D. No. 2. In particular, the term "homologue" covers homology with respect to structure and/or function providing the resultant nucleotide sequence codes for a recombinant enzyme having PME activity. With respect to sequence homology (i.e. similarity), preferably there is at least 75%, more preferably at least 85%, more preferably at least 90% homology. More preferably there is at least 95%, more preferably at least 98%, homology.

In a preferred aspect the terms "variant", "homologue" or "fragment" in relation to the nucleotide sequence coding for the recombinant enzyme of the present invention include any substitution of, variation of, modification of, replacement of, deletion of or addition of one (or more) nucleic acid from or to the sequence sequence shown as SEQ I.D. No. 1 providing the resultant nucleotide sequence codes for a recombinant enzyme having PME activity, preferably having at least the same activity of a recombinant enzyme comprising the sequence shown as SEQ I.D. No. 2. In particular, the term "homologue" covers homology with respect to structure and/or function providing the resultant nucleotide sequence codes for a recombinant enzyme having PME activity. With respect to sequence homology (i.e. similarity), preferably there is at least 75%, more preferably at least 85%, more preferably at least 90% homology. More preferably there is at least 95%, more preferably at least 98%, homology.

The above terms are synonymous with allergic variations of the sequences.

As indicated above, the present invention concerns the sequence presented in the attached sequence listings, or a variant, derivative or homologue thereof.

Preferably, the variant, derivative or homologue can have at least 75% sequence homology (i.e. identity) with any one or more of the sequences presented.

In particular, the term "homology" as used herein may be equated with the term "identity".

Here, sequence homology can be determined by a simple "eyeball" comparison of any one or more of the sequences with another sequence to see if that other sequence has at least 75% identity to the sequence(s).

Relative sequence homology (i.e. sequence identity) can also be determined by commercially available computer programs that can calculate % homology between two or more sequences. A typical example of such a computer program is CLUSTAL.

Sequence homology (or identity) may moreover be determined using any suitable homology algorithm, using for example default parameters. Advantageously, the BLAST algorithm is employed, with parameters set to default values. The BLAST algorithm is described in detail at http://www.ncbi.nih.gov/BLAST/blast_help.html, which is incorporated herein by reference. The search parameters are defined as follows, and are advantageously set to the defined default parameters.

Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (see http://www.ncbi.nih.gov/BLAST/blast_help.html) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al (1994) Nature Genetics 6:119–129.

The five BLAST programs available at http://www.ncbi.nlm.nih.gov perform the following tasks:

blastp compares an amino acid query sequence against a protein sequence database;

blastn compares a nucleotide query sequence against a nucleotide sequence database;

blastx compares the six-frame conceptual translation products of a nucleotide query sequence (both strands) against a protein sequence database;

tblastn compares a protein query sequence against a nucleotide sequence database dynamically translated in all six reading frames (both strands).

tblastx compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149–163, or segments consisting of short-periodicity internal repeats, as determined by the XNU program of Claverie & States (1993) Computers and Chemistry 17:191–201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g. "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect.

Furthermore, in some cases, sequences are masked in their entirety, indicating that the statistical significance of any matches reported against the unfiltered query sequence should be suspect.

NCBI-gi Causes NCBI gi identifiers to be shown in the output, in addition to the accession and/or locus name.

For some applications, preferably sequence comparisons are conducted using the simple BLAST search algorithm provided at http://www.ncbi.nlm.nih.gov/BLAST.

Should Gap Penalties be used when determining sequence identity, then preferably the following parameters are used:

| FOR BLAST | | | |
| --- | --- | --- | --- |
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 10 | 10 | |
| GAP EXTENSION | 0.1 | 0.1 | |

Other computer program methods to determine identify and similarity between the two sequences include but are not limited to the GCG program package (Devereux et al 1984 Nucleic Acids Research 12: 387 and FASTA (Atschul et al 1990 J Molec Biol 403–410).

The present invention also encompasses nucleotide sequences that are complementary to the sequences presented herein, or any derivative, fragment or derivative thereof. If the sequence is complementary to a fragment thereof then that sequence can be used a probe to identify similar coding sequences in other organisms etc.

The present invention also encompasses nucleotide sequences that are capable of hybridising to the sequences presented herein, or any derivative, fragment or derivative thereof.

The present invention also encompasses nucleotide sequences that are capable of hybridising to the sequences that are complementary to the sequences presented herein, or any derivative, fragment or derivative thereof.

The term "complementary" also covers nucleotide sequences that can hybridise to the nucleotide sequences of the coding sequence.

The term "variant" also encompasses sequences that are complementary to sequences that are capable of hydridising to the nucleotide sequences presented herein.

Preferably, the term "variant" encompasses sequences that are complementary to sequences that are capable of hydridising under stringent conditions (eg. 65° C. and 0.1× SSC {1×SSC=0.15 M NaCl, 0.015 Na$_3$ citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

The term "hybridization" as used herein shall include "the process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach C W and G S Dveksler (1995, PCR Primer, a Laboratory Manual, Cold Spring Harbor Press, Plainview N.Y.).

Also included within the scope of the present invention are polynucleotide sequences that are capable of hybridizing to the nucleotide sequences presented herein under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm–5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

In a preferred aspect, the present invention covers nucleotide sequences that can hybridise to the nucleotide sequence of the present invention under stringent conditions (e.g. 65° C. and 0.1×SSC).

The term "nucleotide" in relation to the present invention includes genomic DNA, cDNA, synthetic DNA, and RNA. Preferably it means DNA, more preferably cDNA for the coding sequence of the present invention.

The term "construct"—which is synonymous with terms such as "conjugate", "cassette" and "hybrid"—includes the nucleotide sequence according to the present invention or, the case of the combination of constructs, the GOI directly or indirectly attached to a promoter. An example of an indirect attachment is the provision of a suitable spacer group such as an intron sequence such as the Sh1-intron or the ADH intron, intermediate the promoter and the nucleotide sequence of the present invention or the GOI. The same is true for the term "fused" in relation to the present invention which includes direct or indirect attachment. In each case, the terms do not cover the natural combination of the gene coding for the enzyme ordinarily associated with the wild type gene promoter and when they are both in their natural environment.

The construct may even contain or express a marker which allows for the selection of the genetic construct in, for example, a filamentous fungus, preferably of the genus Aspergillus, such as *Aspergillus niger*, or plants, such as potatoes, sugar beet etc., into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

The term "vector" includes expression vectors and transformation vectors.

The term "expression vector" means a construct capable of in vivo or in vitro expression.

The term "transformation vector" means a construct capable of being transferred from one species to another—such as from an *E.coli* plasmid to a filamentous fungus, preferably of the genus Aspergillus. It may even be a construct capable of being transferred from an *E. coli* plasmid to an Agrobacterium to a plant.

The term "tissue" includes tissue per se and organ.

The term "organism" in relation to the present invention includes any organism that could comprise the nucleotide sequence coding for the recombinant enzyme according to the present invention and/or products obtained therefrom, wherein a promoter can allow expression of the nucleotide sequence according to the present invention when present in the organism.

Preferably the organism is a filamentous fungus, preferably of the genus Aspergillus, more preferably *Aspergillus niger*.

The term "transgenic organism" in relation to the present invention includes any organism that comprises the nucleotide sequence coding for the recombinant enzyme according to the present invention and/or products obtained therefrom, wherein the promoter can allow expression of the nucleotide sequence according to the present invention within the organism. Preferably the nucleotide sequence is incorporated in the genome of the organism.

Preferably the transgenic organism is a filamentous fungus, preferably of the genus Aspergillus, more preferably *Aspergillus niger*.

Therefore, the transgenic organism of the present invention includes an organism comprising any one of, or combinations of, a promoter, the nucleotide sequence coding for the recombinant enzyme according to the present invention, constructs according to the present invention (including combinations thereof), vectors according to the present invention, plasmids according to the present invention, cells according to the present invention, tissues according to the present invention or the products thereof.

The term "transgenic organism" does not cover the native nucleotide coding sequence according to the present invention in its natural environment when it is under the control of its native promoter which is also in its natural environment. In addition, the present invention does not cover the native enzyme according to the present invention when it is in its natural environment and when it has been expressed by its native nucleotide coding sequence which is also in its natural environment and when that nucleotide sequence is under the control of its native promoter which is also in its natural environment.

The transformed cell or organism could prepare acceptable quantities of the desired compound which would be easily retrievable from, the cell or organism.

Preferably the construct of the present invention comprises the nucleotide sequence of the present invention and a promoter.

The term "promoter" is used in the normal sense of the art, e.g. an RNA polymerase binding site.

In one aspect, the nucleotide sequence according to the present invention is under the control of a promoter that may be a cell or tissue specific promoter. If, for example, the organism is a plant then the promoter can be one that affects expression of the nucleotide sequence in any one or more of tuber, stem, sprout, root and leaf tissues.

By way of example, the promoter for the nucleotide sequence of the present invention can be the α-Amy 1 promoter (otherwise known as the Amy 1 promoter, the Amy 637 promoter or the α-Amy 637 promoter) as described in our co-pending UK; patent application No. 9421292.5 filed Oct. 21, 1994. Alternatively, the promoter for the nucleotide sequence of the present invention can be the α-Amy 3 promoter (otherwise known as the Amy 3 promoter, the Amy 351 promoter or the α-Amy 351 promoter) as described in our co-pending UK patent application No. 9421286.7 filed Oct. 21, 1994.

The promoter could additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the nucleotide sequence of the present invention or, in the case of the combination of constructs, the GOI. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

In addition the present invention also encompasses combinations of promoters and/or nucleotide sequences coding for proteins or recombinant enzymes and/or elements.

The present invention also encompasses the use of promoters to express a nucleotide sequence coding for the recombinant enzyme according to the present invention or the GOI, wherein a part of the promoter is inactivated but wherein the promoter can still function as a promoter. Partial inactivation of a promoter in some instances is advantageous. In particular, with the Amy 351 promoter mentioned earlier it is possible to inactivate a part of it so that the partially inactivated promoter expresses the nucleotide of the present invention or a GOI in a more specific manner such as in just one specific tissue type or organ.

The term "inactivated" means partial inactivation in the sense that the expression pattern of the promoter is modified but wherein the partially inactivated promoter still functions as a promoter. However, as mentioned above, the modified promoter is capable of expressing the nucleotide of the present invention or a GOI in at least one (but not all) specific tissue of the original promoter. One such promoter is the Amy 351 promoter described above. Examples of partial inactivation include altering the folding pattern of the promoter sequence, or binding species to parts of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part. Another modification is to mutate the binding sites for regulatory proteins for example the CreA protein known from filamentous fungi to exert carbon catabolite repression, and thus abolish the catabolite repression of the native promoter.

The term "GOI" with reference to the combination of constructs according to the present invention means any gene of interest. A GOI can be any nucleotide that is either foreign or natural to the organisin (e.g. filarnentous fungus preferably of the genus Aspergillus, or a plant) in question. Typical examples of a GOI include genes encoding for proteins and enzymes that modify metabolic and catabolic processes. The GOI may code for an agent for introducing or increasing pathogen resistance. The GOI may even be an antisense construct for modifying the expression of natural transcripts present in the relevant tissues. The GOI may even code for a non-native protein of a filamentous fungus, preferably of the genus Aspergillus, or a compound that is of benefit to animals or humans.

Examples of GOIs include other pectinases, galactonases, pectin depolymerases, polygalacturonases, pectate lyases, pectin lyases, rhamno-galacturonases, hemicellulases, endo-β-glucanases, arabinases, or acetyl esterases, or combinations thereof, as well as antisense sequences thereof.

These other types of enzymes can be added at the same time as the PME or, alternatively, prior to or after the addition of the PME.

By way of example, the GOI can be a PME as disclosed in WO-A-97/03574 or the PME disclosed in either WO-A-94/25575 or WO-A-97/31102 as well as variants, derivatives or homologues of the sequences disclosed in those patent applications.

The GOI may be a protein giving nutritional value to a food or crop. Typical examples include plant proteins that can inhibit the formation of anti-nutritive factors and plant proteins that have a more desirable amino acid composition (e.g. a higher lysine content than a non-transsenic plant). The GOI may even code for an enzyme that can be used in food processing such as chymosin, thaumatin and α-galactosidase. The GOI can be a gene encoding for any one of a pest toxin, an antisense transcript such as that for patatin or α-amylase, ADP-glucose pyrophosphorylase (e.g. see EP-A-0455316), a protease antisense, a glucanase or genomic PME.

The GOI may even code for an intron of a particular enzyme but wherein the intron can be in sense or antisense orientation. In the latter instance, the particular enzyme could be genomic PME. Antisense expression of enomic exon or intron sequences as the GOI would mean that the natural PME expression would be reduced or eliminated but wherein the recombinant PME expression would not be affected. This is particularly true for antisense intron or sense intron expression.

The GOI can be the nucleotide sequence coding for the α-amylase enzyme which is the subject of our co-pending UK patent application 9413439.2 filed on Jul. 4, 1994. The GOI can be the nucleotide sequence coding for the α-amylase enzyme which is the subject of our UK patent application 9421290.9 filed on Oct. 21, 1994. The GOI can be any of the nucleotide sequences coding for the ADP-glucose pyrophosphorylase enzymes which are the subject of our PCT patent application PCT/EP94/01082 filed Apr. 7, 1994. The GOI can be any of the nucleotide sequences coding for the α-glucan lyase enzyme which are described in our PCT patent application PCT/EP94/03397 filed Oct. 15, 1994.

The host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the gene may need to be suitably modified before transformation—such as by removal of introns.

As mentioned above, a preferred host organism is of the genus Aspergilus, such as *Aspergillus niger*.

A transsgenic Aspergillus according to the present invention can be prepared by following the teachings of Rambosek, J. and Leach, J. 1987 (Recombinant DNA in filamentous fungi: Progress and Prospects, CRC Crit. Rev. Biotechnol. 6:357–393), Davis R. W. 1994 (Heterologous gene expression and protein secretion in Aspergillus. In: Martinelli S. D., Kinghorn J. R.(Editors) Aspergilius: 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In: Leong, S. A., Berka R. M. (Editors) Molecular Industrial Mycology. Systems and Applications for Filamentous Fungi. Marcel Dekker Inc. New York 1991. pp 1–29) and Turner G. 1994 (Vectors for genetic manipulation. In: Martinelli S. D. Kinghorn J. R.(Editors) Aspergillus: 50 years on. Progress in industrial microbiology vol 29. Elsevier Amsterdam 1994. pp. 641–666). However, the following commentary provides a summary of those teachings for producing transgenic Aspergillus according to the present invention.

For almost a century, filamentous fungi have been widely used in many types of industry for the production of organic compounds and enzymes. For example, traditional japanese koji and soy fermentations have used Aspergillus sp. Also, in this century *Aspergillus niger* has been used for production of organic acids particular citric acid and for production of various enzymes for use in industry.

There are two major reasons why filamentous fungi have been so widelyused in industry. First filamentous fungi can produce high amounts of extracelluar products, for example enzymes and organic compounds such as antibiotics or organic acids. Second filamentous fungi can grow on low cost substrates such as grains, bran, beet pulp etc. The same reasons have made filamentous fungi attractive organisms as hosts for heterologous expression according to the present invention.

In order to prepare the transgenic Aspergillus, expression constructs are prepared by inserting the nucleotide sequence according to the present invention (or even the GOI) into a construct designed for expression in filamentous fungi.

Several types of constructs used for heterologous expression have been developed. These constructs preferably contain a promoter which is active in fungi. Examples of promoters include a fungal promoter for a highly expressed extracelluar enzyme, such as the glucoamylase promoter or the α-amylase promoter. The nucleotide sequence according to the present invention (or even the GOI) can be fused to a signal sequence which directs the protein encoded by the nucleotide sequence according to the present invention (or even the GOI) to be secreted. Usually a signal sequence of fungal origin is used. A terminator active in fungi ends the expression system.

Another type of expression system has been developed in fungi where the nucleotide sequence according to the present invention (or even the GOI) can be fused to a smaller or a larger part of a fungal gene encoding a stable protein. This can stabilize the protein encoded by the nucleotide sequence according to the present invention (or even the GOI). In such a system a cleavage site, recognized by a specific protease, can be introduced between the fungal protein and the protein encoded by the nucleotide sequence according to the present invention (or even the GOI), so the produced fusion protein can be cleaved at this position by the specific protease thus liberating the protein encoded by the nucleotide sequence according to the present invention (or even the GOI). By way of example, one can introduce a site which is recognized by a KEX-2 like peptidase found in at least some Aspergilli. Such a fusion leads to cleavage in vivo resulting in protection of the expressed product and not a larger fusion protein.

Heterologous expression in Aspergillus has been reported for several genes coding for bacterial, fungal, vertebrate and plant proteins. The proteins can be deposited intracellularly if the nucleotide sequence according to the present invention (or even the GOI) is not fused to a signal sequence. Such proteins will accumulate in the cytoplasm and will usually not be glycosylated which can be an advantage for some bacterial proteins. If the nucleotide sequence according to the present invention (or even the GOI) is equipped with a signal sequence the protein will accumulate extracelluarly.

With regard to product stability and host strain modifications some heterologous proteins are not very stable when they are secreted into the culture fluid of fungi. Most fungi produce several extracelluar proteases which degrade heterologous proteins. To avoid this problem special fungal strains with reduced protease production have been used as host for heterologous production.

For the transformation of filamentous fungi, several transformation protocols have been developed for many filamentous fungi (Ballance 1991, ibid). Many of them are based on preparation of protoplasts and introduction of DNA into the protoplasts using PEG and $Ca^{2+}$ ions. The transformed protoplasts then regenerate and the transformed fungi are selected using various selective markers. Among the markers used for transformation are a number of auxotrophic markers such as argB, trpC, niaD and pyrG, antibiotic resistance markers such as benomyl resistance, hygromycin resistance and phleomycin resistance. A commonly used transformation marker is the amds gene of *A. nidulans* which in high copy number allows the fungus to grow with acrylamide as the sole nitrogen source.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275. 104): and Ito. H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant.

Even though the enzyme and the nucleotide sequence coding therefor are not disclosed in EP-B-0470145 and CA-A-2006454, those two documents do provide some useful background commentary on the types of techniques that may be employed to prepare transgenic plants according to the present invention. Some of these background teachings are now included in the following commentary.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

Thus, in one aspect, the present invention relates to a vector system which carries a nucleotide sequence or construct according to the present invention and which is capable of introducing the nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* An et al. (1986), *Plant Physiol.* 81, 301–305 and Butcher D. N. et al. (1980), *Tissue Culture Methods for Plant Pathologists*, eds.: D. S. Ingrams and J. P. Helgeson, 203–208.

Several different Ti and Ri plasmids have been constructed which are suitable for the construction of the plant or plant cell constructs described above. A non-limiting example of such a Ti plasmid is pGV3850.

The nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct. Preferably, the vector system is an *Agrobacterium tumefaciens* Ti-plasmid or an *Agrobacterium rhizogenes* Ri-plasmid or a derivative thereof, as these plasmids are well-known and widely employed in the construction of transgenic plants, many vector systems exist which are based on these plasmids or derivatives thereof.

In the construction of a transgenic plant the nucleotide sequence or construct of the present invention may be first constructed in a microorganism in which the vector can replicate and which is easy to manipulate before insertion into the plant. An example of a useful microorganism is *E. coli.*, but other microorganisrns having the above properties may be used. When a vector of a vector system as defined above has been constructed in *E. coli.* it is transferred, if necessary, into a suitable Agrobacterium strain, e.g. *Agrobacterium tumefaciens*. The Ti-plasmid harbouring the nucleotide sequence or construct of the invention is thus preferably transferred into a suitable Agrobacterium strain, e.g. *A. tumefaciens*, so as to obtain an Agrobacterium cell harbouring the nucleotide sequence or construct of the invention, which DNA is subsequently transferred into the plant cell to be modified.

As reported in CA-A-2006454, a large amount of cloning vectors are available which contain a replication system in *E. coli* and a marker which allows a selection bf the transformed cells. The vectors contain for example pBR 322, the pUC series, the M13 mp series, pACYC 184 etc.

In this way, the nucleotide or construct of the present invention can be introduced into a suitable restriction position in the vector. The contained plasmid is used for the transformation in *E.coli*. The *E.coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After each introduction method of the desired promoter or construct or nucleotide sequence according to the present invention in the plants the presence and/or insertion of further DNA sequences may be necessary. If, for example for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985. Chapter V; Fraley. et al., Crit. Rev. Plant Sci., 4:1–46; and An et al., EMBO J. (1985) 4:277–284.

Direct infection of plant tissues by Agrobacterium is a simple technique which has been widely employed and which is described in Butcher D. N. et al. (1980). *Tissue Culture Methods for Plant Pathologists*, eds.: D. S. Ingrams and J. P. Helgeson. 203–208. For further teachings on this topic see Potrykus (Annu Rev Plant Physiol Plant Mol Biol [1991] 42:205–225) and Christou (Agro-Food-Industry Hi-Tech March/April 1994 17–27). With this technique, infection of a plant may be done on a certain part or tissue of the plant, i.e. on a part of a leaf, a root, a stem or another part of the plant.

Typically, with direct infection of plant tissues by Agrobacterium carrying the promoter and/or the GOI, a plant to be infected is wounded, e.g. by cutting the plant with a razor or puncturing the plant with a needle or rubbing the plant with an abrasive. The wound is then inoculated with the Agrobacterium. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

The process of the present invention can occur ex vivo or even in vivo—such as in planta. In the latter respect, the plant may be a transgenic plant, such as a plant that has been genetically engineered to produce different levels and/or types of pectin. The plant may also be plant material, rather than a whole plant. Here, the plant material may be obtained from a transgenic plant, such as a plant that has been genetically engineered to produce different levels and/or types of pectin. The plant or plant material may be or may be derived from a vegetable, a fruit or other type of pectin containing or producing plant. Here, the vegetable material and/or the fruit material can be a mash.

In summation, the present invention provides a process for treating a pectin with a pectin methyl esterase (PME); wherein the PME is not a plant PME; but wherein the PME is capable of exhibiting at least one plant PME property; and wherein the at least one plant PME property comprises at least block-wise de-esterification of the pectin.

PME activity itself can be determined quite readily. A protocol for determining PME activity is presented after the Examples Section.

The purity of the PME fraction can be investigated by SDS-PAGE using Pharmacia PhastSystem™ with 10–15% SDS-gradient gels. Electrophoresis and silver staining of the proteins can be done as described by the manuals from Pharmacia. For determination of pI IEF 3–9 PhastSystem™ gels can be used.

Immuno gel electrophoresis can be used for characterisation of antibodies (see later section)—such as polyclonal antibodies—raised against PME. The enzyme fractions are then separated on SDS-PAGE and transferred to NC-paper by semi-dry blotting technique on a Semidry transfer unit of the PhastSystem™. The NC-paper is incubated with the primer antibody diluted 1:50 and stained with the second antibody coupled to alkaline phosphatase (Dako A/S Glsotrup, Denmark) used in a dilution of 1:1000.

Further studies that can be performed on the PME include peptide mapping. In this respect, PME can be digested with either trypsin or endo-proteinase Lys-C from *Lysobacter enzymogenes* (both enzyme preparations should be are sequencing grade)—which can be purchased from Boerhinger Mannheim, Germany.

Typically, 100 mg purified PME is carboxy methylated with iodoacetamide to protect the reduced SH-groups. Then the protein is cleaved with trypsin (4 mg/20–100 ml). The hydrolytic cleavage is performed at 40° C. for 2×3 hrs. The reaction is stopped with addition of 20 ml TFA. After centrifugation at 15,000 rpm for 5 min the peptides are purified on a reverse-phase HPLC column (Vydac 10 C18 column). 2×500 ml samples are applied. The peptides are eluted and separated with an increasing acetonitrile gradient from 0.05–0.35% in 60 min in 0.1% TFA. The peptides are collected manually in Eppendorf tubes.

For digestion with endo-proteinase Lys-C, freeze dried PME (0.1 mg) is dissolved in 50 ml of 8 M urea, 0.4 M $NH_4HCO_3$, pH 8.4. After overlay with $N_2$ and addition of 5 ml of 45 mM DTT, the protein is denatured and reduced for 15 min at 50° C. under $N_2$. After cooling to room temperature, 5 ml of 100 mM iodoacetamide is added for the cysteines to be derivatised for 15 min at room temperature in the dark under $N_2$. Subsequently, 90 ml of water and 5 mg of endo-proteinase Lys-C in 50 ml 50 mM tricine and 10 mM EDTA, pH 8.0, are added and the digestion was carried out for 24 hrs at 37° C. under $N_2$.

The resulting peptides are then separated as described for trypsin digested peptides.

Selected peptides can be further purified on a Devosil 3 $C_{18}$ RP-HPLC column 0.46×10 cm (Novo Nordisk, Denmark). The purified peptides are then applied on an amino acid sequencer, Applied Biosystems 476A, using pulsed-liquid fast cycles.

Antibodies can be raised against the enzyme of the present invention by injecting rabbits with the purified enzyme and isolating the immunoglobulins from antiserum according to procedures described according to N Harboe and A Ingild ("Immunization, Isolation of Immunoglobulins, Estimation of Antibody Titre" In A Manual of Quantitative Immunoelectrophoresis, Methods and Applications, N H Axelsen, et al (eds.), Universitetsforlaget. Oslo, 1973) and by T G Cooper ("The Tools of Biochemistry", John Wiley & Sons, New York, 1977).

Figure 2:
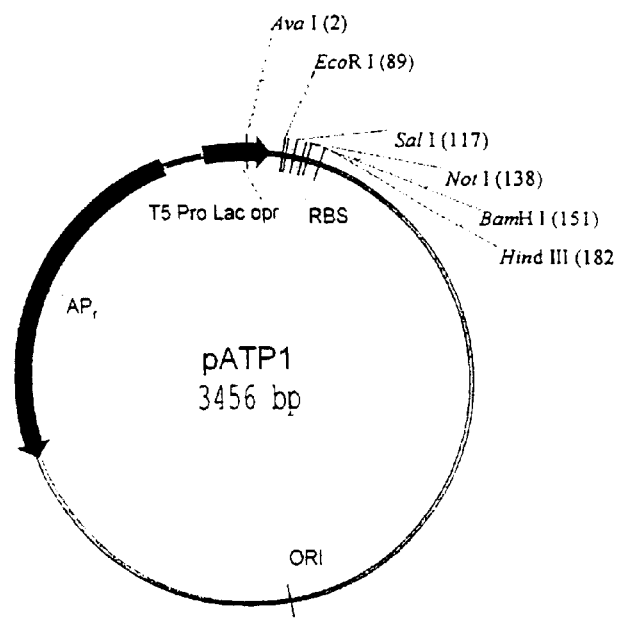
Figure 3:
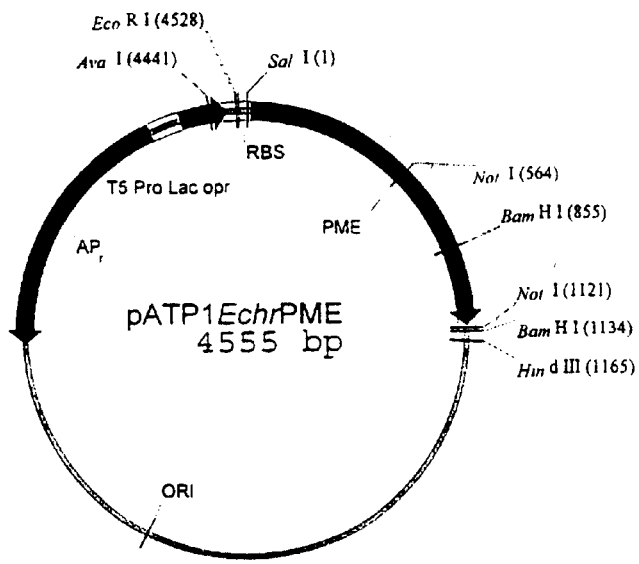
Figure 4:
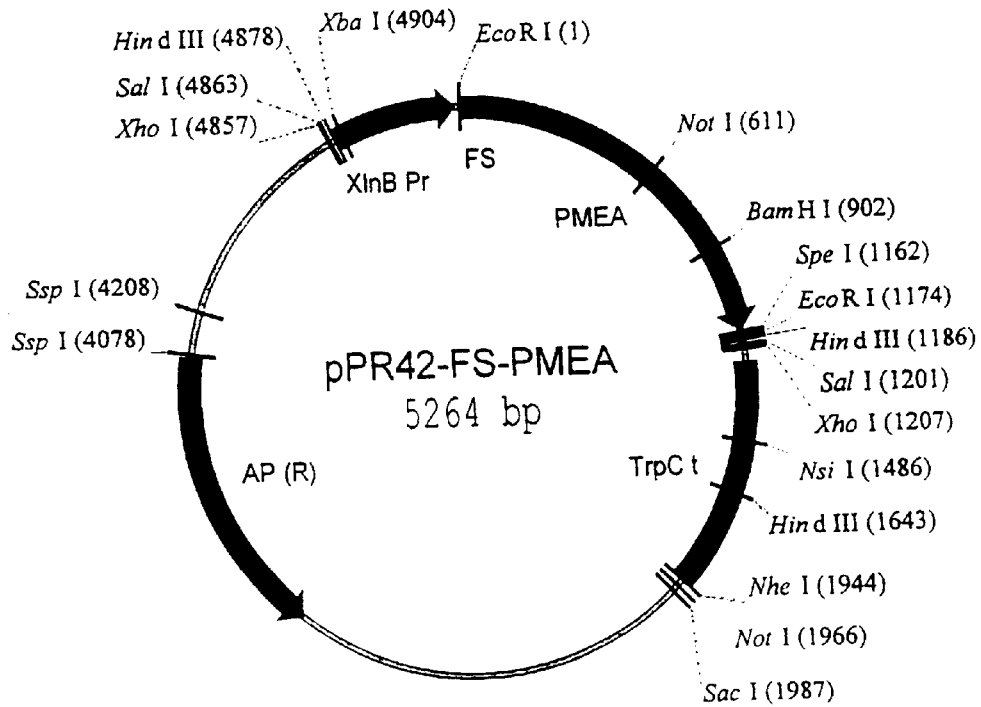
Figure 5:
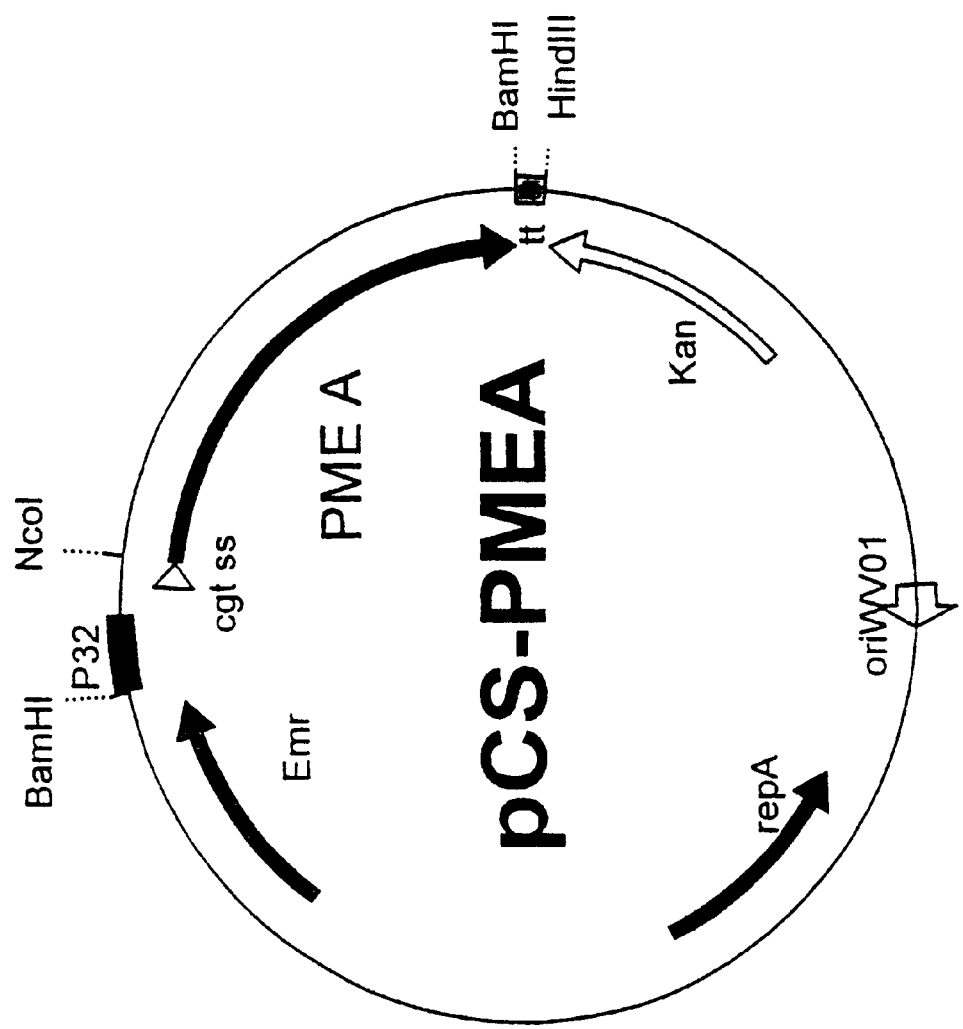

The present invention will now be described only by way of example, in which reference is made to the following attached Figures:

FIG. 1—which is a representation of a plasmid,
FIG. 2—which is a representation of a plasmid,
FIG. 3—which is a representation of a plasmid,
FIG. 4—which is a representation of a plasmid, and
FIG. 5—which is a representation of a plasmid.

EXPERIMENTAL SECTION

Cloning of the *Erwinia chrysanthemi* PME Gene
Materials
*Erwinia chrysanthemi* (PD97) ("*E.chr.*") was purchased from Culture Collection of Plant Protection Service (PD) Wageningen, the Netherlands.
Growth of the Erwinia strain.
The strain was grown in LB-media at 30° C.

DNA
Genomic DNA was isolated from the strain using Qiagen RNA/DNA kit (Qiagen).
PCR
Genomic DNA was used as template.

Primers to clone the PME gene from *Erwinia chrysanthemi* was designed from the published nucleotide sequence of the *Erwinia chrysanthemi* B374 PME gene, accessed from the EMBL/GenBank Data Libraries (accession number Y00549).

*Erwinia chrysanthemi* PCR primers

PME 5' end primer: 5'-AGTCGACGTGTATGTTAAA AACGATCTCTGG-3' (SEQ ID NO:4)
PME 3' end primer: 5'-A<u>GCGGCCGC</u>AATTCG TCAGGGTAATGTCGG-3 (SEQ ID NO:5)

The 5' end primers contain a SalI enzyme restriction site, which is Written in italic and the 3' end primers contain a NotI enzyme restriction site, which is underlined, in order to facilitate cloning of the amplified gene into expression vectors.

PCR was performed with the Expand High Fidelity PCR system (Boehringer Mannheim) according to the manufactures instructions with the following temperature cycling:

| 95° C. | 3 min in 1 cycle |
|---|---|
| 94° C. | 15 sec |
| 50° C. | 30 sec |
| 68° C. | 3 min in 10 cycles |
| 94° C. | 15 sec |
| 57° C. | 30 sec |
| 68° C. | 3 min and additional 20 sec pr. cycle in 20 cycles |

Cloning of PCR Fragments

PCR fragments were cloned into the PCR 2.1-TOPO cloning vector (Invitrogern), as described by the manufacturer.

DNA Sequencing.

Double stranded DNA was sequenced essentially according to the dideoxy method of Sanger et al (1979) using the Thermo Sequenase fluorescent labelled primer cycle sequencing kit with 7-deaza-dGTP (Amnersham Pharmacia Biotech), 5'Cy5-labelled primers and the Pharmacia LKB A.L.F. DNA sequencer (Ref: Sanger, F., Nicklen. S., and Coulson A. R. (1979) DNA sequencing with chain-determination inhibitors. Proc. Nat. Acad. Sci. USA 74: 5463–5467). The primers used for sequencing are listed below, presented 5' to 3':

UNI (M13–20 primer)—17 mer
   Cy5-GTAAACGACGGCCAGT (SEQ ID NO:8)
REV—19 mer
   Cy5-GGAAACAGCTATGACCATG (SEQ ID NO:7)
*E.chr* PME—01 17 mer
   Cy5-GATTATCCATGCTGGTG (SEQ ID NO:8)
*Erwinia chrysanthemi* PME—02 18 mer
   Cy5-CGGCGTCTATAATGAACG (SEQ ID NO:9)
*Erwinia chrysanthemi* PME—03 16 mer (SEQ ID NO:10)
   Cy5-GCGACAGCGACAGCAG
*Erwinia chrysanthemi* PME—04 19 mer
   Cy5-CCGTGGCAGCCGCAATGAC (SEQ ID NO:11)

The sequenced nucleotide sequence of the PME gene is shown in the attached sequence listings.

EXPRESSION OF THE *Erwinia chrysanthemi* PME GENE IN *E.coli*

Generation of the expression vector pATP1:

pATP1 was generated by modifying the pQE60 expression vector from Qiagen in order to use the cloned genes own translation start site and to avoid the histidine tag. The pQE60 expression vector is shown in FIG. 1.

The 64 bp EcoRI-HindIII fragment was excised from the pQE60 expression vector and replaced with the 50bp EcoRI-BamHI fragment from the pSPORT1 vector (Gibco/BRL), to introduce more enzyme restriction sites.

50 bp pSPORT1 EcoRI-HindIII fragment:

5' AAGCTTGGATCCTCTAGAGCGGCCGC-CGACTAGTGAGCTCGTCGACCCGGAATTC 3' (SEQ ID NO:12)

The EcoRI enzyme restriction site is underlined and the HindIII enzyme restriction site is written in bold and italic letters.

The 10 bp EcoRI-SalI fragment within the 50 bp fragment obtained from the pSPORT1 vector, was replaced with a 28 bp EcoRI-SalI fragment containing a Ribosome Binding Site (RBS) and thereby creating expression vector pATP1, see FIG. 2.

Generation of the 28 bp EcoRI-SalI fragment by annealing of two oligo nucleotides:

RBS primer 1

5' CACACA<u>GAATTC</u>ATTAAAGAGGAGAAAT TAACCCGTCGACCCGGGAG 3' (SEQ ID NO:13)

RBS primer 2:

5' CTCCCGGGTCGACGGGTTAATTTCTC-CTCTTTAATGAATTCTGTGTG 3' (SEQ ID NO:14)

EcoRI enzyme restriction site is underlined

SalI enzyme restriction site is written in italic letters

The Ribosome Binding Site (RBS) is written in bold letters

The cloned PME gene from *Erwinia chrysanthemi* was excised from the PCR2.1 TOPO vector at the SalI and NotI sites, located in the primers used to PCR clone the genes. The SalI-NotI gene fragments were recloned into the pATP1 expression vector, pATP1*E.chr*.PME (FIG. 3).

Transformation of pATP1*E.chr*.PME vector into M15/pREP4 competent cells.

The pATP1*E.chr*.PME vector was transformed into competent M15/pREP4 cells as described by the manufacturer (Qiagen).

Colonies containing the pATP1*E.chr*.PME vector were selected and used for induction of expression of the *Erwinia chrysanthemi* PME gene.

Growth of *E.coli*

*E.coli* transformed with pATP1*EchrPME* vector was grown in LB-medium+100 µg/ml ampicillin and 25 µg/ml kanamycin over night at 37° C. and 20 ml pre-culture was added to 800 ml LB-medium 100 µg/ml ampicillin and 25 µg/ml kanamycin and incubated at 37° C. In total 3×800 ml was prepared. The cells were grown to the absorption at 600 nm was 0.7. 800 µl 1M IPTG was added and after 4 hrs incubation at 37° C. the cells were harvested.

Preparation of Cell Free Extract

The cells were harvested by centrifugation at 10000 rpm for 10 min and resuspended in 50 ml extraction buffer (50 mM MES pH 6.8). The cells were disrupted by sonication for 4×3 min with duty cycle of 70%. In between and during the sonication treatment the sample was stored on ice. The PME fraction (the supernatant) was obtained after centrifugation at 10000 rpm for 10 mm.

Chromatography

The PME was purified according to the following procedure. All operations were performed at 4° C. The supernatant obtained as described above was separated by cation exchange chromatography. A 50 ml sample was applied to a CM-Sepharose™CL-6B (50 ml column material) and washed with buffer A: 50 mM MES pH 6.8. The majority of the proteins did not bind to the column but the PME was absorbed and after washing off the unbound proteins with buffer A the bound proteins were eluted with an increasing NaCl gradient from 0–1 M NaCl in total 450 ml. The flow was 0.5 ml/min and fractions of 2.5 ml were collected. The protein absorption profile was measured at 280 nm.

All fractions were analysed for PME activity and protein. The protein content was measured spectrophotometrically with the BioRad method.

The fractions containing PME activity were pooled and used as enzyme extract for enzymatic PME treatment of pectin. SDS-PAGE revealed that this partially purified *E. chrysanthemi* PME fraction only contained 3–4 proteins.

In order to purify the PME to homogeneity 1 ml of the pooled fraction was concentrated by dialysis using Centricon filter system. Buffer exchange to 50 mM Tris, 0.1M NaCl pH 7 was done on the same system. 200 µl concentrated sample was then applied to a Sephacryl™S-200 (2.6×70 cm) gel filtration column. The column was equilibrated with 50 mM Tris, 0.1 M NaCl pH 7. The flow was 0.5 ml/min and fractions of 0.5 ml were collected.

The fractions containing PME activity were pooled and concentrated using Centricon as described above. The concentrated sample was then applied to a Superdex™ G-75 which was equilibrated with 50 ml Tris, 0.1 M NaCl pH 7. The now was 0.5 ml/min and fractions of 2 ml were collected. The fractions containing PME activity were pooled and concentrated.

Enzyme Activity

PME catalyses the cleavage of methylester groups from pectin. During the purification steps PME was detected by a fast method using methyl red indicator test. Due to cleavage of methyl groups from galacturonic residues in the pectin chain, carboxyl groups were formed and the pH drops in the assay. The pH indicator—methyl red—changes colour at pH drop from yellow (pH 6.2) to pink (pH 4.2). The assay contained 1 ml 0.5% lime pectin (DE 70%) solubilized in 0.15 M NaCl pH 7 and 25 µl sample. The samples which showed positive methyl red test after 10 min incubation at 30° C. were then further measured by the titration method. (Versteeg et al. (1978) Lebensmittel.-Wiss. u. Technol., 11: 267–274)

With the titration method the assay contained 10 ml 0.5% lime pectin solubilized in 0.15 M NaCl pH 6.8 and 10–100 µl sample. Titration was performed with 0.02 M NaOH and the reaction was measured at room temperature. An automatic titrator was used. (Versteeo et al. (1978) Lebensmittel.-Wiss. u. Technol., 11: 267–274)

SDS-PAGE/Western Blotting

The purity of the PME fraction was investigated by SDS-PAGE as discussed above.

Antibody Production

Antibodies are raised against the enzyme of the present invention by injecting rabbits with the purified enzyme and isolating the immunoglobulins from antiserum according to procedures described according to N Harboe and A Ingild ("Immunization, Isolation of Immunoglobulins, Estimation of Antibody Titre" In A Manual of Quantitative Immunoelectrophoresis, Methods and Applications, N H Axelsen, et al (eds.), Universitetsforlaget, Oslo, 1973) and by T G Cooper ("The Tools of Biochemistry", John Wiley & Sons. New York, 1977).

STUDY EXPERIMENT 1

During purification of PME the cell free extract was applied to a cation exchange column (CM-Sepharose CL-6B). PME binds strongly to a cation exchange column material at pH 6.8 whereas most of the proteins do not bind to the column and so elute in the wash volume. With increasing NaCl gradient PME eluted into one peak (fraction 56–64).

After concentration the PME fraction was further purified using gel filtration chromatogtaphy (Sephacryl S-200 column) and followed by Superdex G-75 gel filtration. Fractions containing the highest PME activity were pooled. The enzyme activity was 65 U/ml.

The fraction was tested for pectin degrading activity by viscosity determination with 1% pectin at pH 4.8. The results showed that after 24 hrs no change in the viscosity was found.

SDS-PAGE showed only one protein band in the purified PME fraction with a MW of 36,000 D. Isoelectric focusing of PME showed that the pI was >9.

Characterization and Kinetic Data

Characterization of PME and optima determinations were all done with the titration method as described in Materials and Methods.

pH optimum of PME activity was measured with 0.5% lime pectin in 0.15 M NaCl. The optimum was found around pH 7. The enzyme has pH optimum at neutral pH but at pH 5 70% of the maximal activity was still measured.

Temperature optimum was found at 48° C.

The temperature stability of PME was determined by incubating the enzyme sample in Eppendorf tubes at various temperatures for 15 min. After incubation the enzyme activity was measured by traditional assay by titric method. The stability of the enzyme activity was between 20°–50° C. Incubation for 15 min at 60° C. resulted in inactivation of the enzyme.

The affinity for lime pectin was determined by Hanes plot of different pectin concentration versus activity. The $k_m$ was calculated from the curye to be 0.44 mg/ml. The km was determined with pectin with DE 70% and the results showed that the km value was in the same range as found for orange PME but was 10 times lower than found for fungal PME from Aspergillus. This means that the catalytic activity of the plant and bacteria enzymes are 10-fold higher than that of the fungal enzyme.

*E. chrysanthemi* PME could also de-esterify sugar beet pectin. The PME activity was measured as described in Materials and Methods except that 1% sugar beet pectin solubilized in 0.15 M NaCl was used in the assay.

We have also found that the enzyme does not necessarily require NaCl for activity. However, the activity is increased with addition of NaCl up to 0.1–0.15 M NaCl. Higher concentrations of NaCl decreases the activity.

STUDY EXPERIMENT 2

Pectin Treated with *E. chrysanthemi* has Similar Properties to Pectin Treated with Plant PME Calcium sensitive pectin The URS pectin was treated with *E. chrysanthemi* PME and the obtained modified pectin was characterized with respect to % DE and Calcium sensitivity (CS).

|  | % DE | CS |
|---|---|---|
| GRINSTED ™ URS Pectin | 81.1% | 1.1 |
| Pectin 2084-124-1 | 73.7% | 2.2 |
| Pectin 2084-124-2 | 70.6% | 14.5 |
| Pectin 2084-125-2 | 66.6% | gel. |
| Pectin 2084-125-1 | 62.8% | gel. |

The two pectins (Pectin 2084-125-2 and Pectin 2084-125-1) gelled with the added calcium in the test because of the very, high Ca-sensitivity and it was therefore not possible to obtain a CS value. This very high Ca-sensitivity is only obtainable with block-wise de-methylated pectins.

Enzymatic fingerprinting of the *E. chrysanthemi* modified pectins by using pectin lyase or polygalacturonase showed that the *E. chrysanthemi* PME de-methylates pectin block-wise producing non polygalacturonic acid like blocks (random blocks).

Effect of *E. Chrysanthemi* PME treated pectin on the viscosity and stability of protein drinks

|  | % DE | SP in acidified milk drink | Viscosity at cP |
|---|---|---|---|
| 2143-17.1 | 78.9% | 0.15% | 10.2 |
| 2143-27 | 77.5% | 0.15% | 10.6 |

SP=The minimum concentration at which the pectin stabilize the acidified milk drink.

De-esterification of the URS pectin from 81% to 78–79% changed the Ca-sensitivity.

The enzymatic modified pectins were tested in the acidified milk drink at the dosage concentrations of 0.1%, 0.15%, 0.175%, 0.2% and 0.25%. The quality of the individual acidified milk drink produced was investigated by the parameters such as whey separation, the sedimentation % and the viscosity.

The results showed that the enzymatic modified pectins stabilize the protein at the low pectin concentration of 0.15%. Each of the samples had a low viscosity. The *E. chrysanthemi* PME modified pectins have lower viscosity at the pectin concentration of 0.15% than the standard commercial stabilizer.

By treating the mother URS pectin with *E. chrysanthemi* PME an unsuitable pectin was made suitable as a stabilizing agent in the acidified milk drink and this treated pectin behave just as well as an excellent commercial stabilizer.

METHODS

Enzymatic Treatment of Pectin with PME from *E. chrysanthemi*

A batch of enzymated pectin was prepared as follows: 45 g pectin was dissolved in hot water under efficient stirring. 15 g NaCl was added and the volume adjusted to 1.8 l with water. This solution was stirred until the salt had dissolved. The pectin solution was cooled to 40° C. and the pH was increased to pH 6.5, using 1 N NaOH and efficient stirring. An appropriate sample of *E. chrysanthemi* PME was added and the enzymatic reaction continued until the desired degree of esterification was achieved. The pH was kept constant at pH 6.5 by automatic dosage of 1 N NaOH during the incubation period, and the enzymatic reaction was followed by the consumption of NaOH.

When the pectin sample had reached the desired degree of esterification the NaOH addition was stopped, the pH of the solution lowered to about 3.0 by addition of 2% HCl. The pectin solution was then heated to 70° C. for 5 min to completely inactivate the enzyme. The treated pectin was precipitated with 1 volume of isopropanol, washed with 60% isopropanol and pressed to about 50% dry matter. The treated pectin batch was then air dried at 40° C. and finally milled to a dry powder.

Determination of Pectin Samples Calcium Sensitivity Index (CS)

Calcium sensitivity was measured by the protocol presented above.

Determination of Pectin Samples Degree of Esterification (%DE)

The degree of esterification was measured by the protocol presented above.

Acidified Milk Drink Test

Standardised skimmed milk (17% MSNF), prepared from mixing powdered milk with. adequate volume of de-ionised water at 68° C. for 20 minutes and cooled down to 30° C., was acidified at 30° C. with 3.3% glucone-delta-lactone (GDL) to about pH 4. The pectin sample was added as a sugar solution and stirred for 30 min. The acidified milk drink was homogenized at 200 bar at room temperature and then filled into sterile 250 ml plastic bottles. It was then heated on a water bath at 75° C. for 10 min with internals of shaking for 5 minutes. Finally, the drink was cooled to room temperature and then stored overnight at 5° C.

Viscosity Determination of the Acidified Milk Drink

The viscosity of a sample of the milk drink was determined using a Brookfield Viscometer 11T at rpm 30. After stirring for 30 sec the viscosity is measured.

Protein Stability Measured by a Centrifugation Test 40 g of a sample (e.g. acidified milk drink) is centrifugated at room temperature at 2300×g for 20 min. The supernatant is discarded and the centrifuge glass placed upside down for 30 min. The glass is weighed and the sedimentation % calculated as follows:

$$\% \text{ Sedimentation} = \frac{\text{Wgt of glass after centri} - \text{Wgt of glass}}{\text{Wgt of sample}} \times 100$$

Where Wgt=weight and centri=centrifugation

Construction of Bacillus Expression Plasmid pCS.

The Bacillus/*E. coli* shuttle vector pDP66K (obtained from Dr L. Dijkhuizen, Rijks. University of Groningen, the Netherlands), was modified to make it suitable for cloning and expression of different genes. Details on the pDP66K vector are described in Penninga D et al (1996). (It is to be noted that any other suitable shuttle vector—such as a commercially available shuttle vector—could also be used in this experiment.) The pCS plasmid was generated by modifying the promoter, the cyclodextrin glycosyl transferase (cgt) signal sequence, deleting the rest of the cyclodextrin glycosyl transferase gene and replacing the transcription terminal sequence. The p32 promoter and cyclodextrin glycosyl transferase signal sequence was modified by PCR to contain a NcoI site at the ATG codon in the 3' end of the signal sequence. The transcription terminator sequence was replaced by a PCR amplified transcription terminator sequence from the pUB110 plasmid (McKenzie, T., Hoshino, T., Tanaka, T. and Sueoka, N. (1986) The nucleotide sequence of pUB110: some salient features in relation to replication and its regulation. *Plasmid* 15 (2), 93–103, and McKenzie, T., Hoshino, T., Tanaka, T. and Sueoka, N. (1987) Correction. A revision of the nucleotide sequence and functional map of pUB110. *Plasmid* 17 (1), 83–85). A 5' BamHI and a 3' HindIII enzyme restriction sites were introduced into the PCR amplified transcription terminator sequence for cloning purposes. The resultant pCS plasmid is shown in FIG. 5.

Generation of the PME Gene Fragments for Cloning into the Bacillus pCS Plasmid.

Two PME gene PCR products were amplified, one containing the full length coding region were the second amino acid was changed from a leucine to a valine in order to introduce a NcoI site at the 5' ATG start codon of the gene for cloning purposes. In the 3' end a BamHI site was introduced for cloning purposes. The second PME gene PCR product was amplified without the genes signal sequence, starting from the alanine amino acid codon at position 25 at the amino acid level. The PCR product was designed to contain a methionine in front of the starting alanine amino acid in order to introduce a NcoI, necessary for cloning purposes. In the 3' end of the PCR product a BamHI site was introduced. PCR amplification of the two PME sequences were verified by DNA sequencing. The two amplified PME sequences were cloned into the pHM plasmid using the NcoI and BamHI restriction enzymes while the PME sequence without the signal sequence also was cloned into the pCS plasmid using the same restriction enzymes.

Expression of the PME Gene in Bacillus.

The four different constructs were transformed into *Bacillus substilis* and cultured in 2 xYT media containing 50 mg/ml kanamycin.

Expression of the *E. chrysanthemi* PME Gene in *Aspergillus niger*.

Construction of the Expression Vector pPR42-FS-PMEA

For expression in *Aspergillus niger* the *E. chrysanthemi* PME gene was furnished with a fungal signal sequence derived from the *Aspergillus niger* PME gene (Khanh, N. Q. et al (1991) Gene 1, 71–77) comprising the following sequence:

*Aspergillus niger* PME signal sequence:
ATGGTTAAGTCAATTCTTGCATCCGT-
TCTCTTTGCGGCGACTGCGCTGGCC (SEQ ID NO:15)
MetValLysSerIleLeuAlaSerVal-
LeuPheAlaAlaThrAlaLeuAla (SEQ ID NO:16)

Three overlapping oligo nucleotide 5' end primers P1, P2 and P3 were used together with a 3' end primer P4 to fuse the fungal signal sequence to the 5' of the coding sequence of the *E. chrysanthemi* PME gene by PCR.

P1: 5'-GCGGCGACTGCGCTGGCCAT GTTAAAAACGATCTCTGGAACCC (SEQ ID NO:17)

P2: 5'-AAGTCAATTCGCATCCGTTCTCMGCG GCGACTGCGC (SEQ ID NO:18)

P3: 5'-TGAATTCTCATGGTTAAGCAAUCTT GCATCCG (SEQ ID NO:19)

P4: 5'-TACTAGTGTCAGGGTAATGTCGGC (SEQ ID NO:20)

The 5' end primer P1 contains the 5' end of the *E. chrysanthemi* PME coding sequence, underlined. The 5' end primer P3 contains an EcoRI restriction enzyme site, underlined, and the 3' end primer P4 contains a SpeI restriction enzyme site, underlined, to facilitate cloning.

PCR was performed with the Expand High Fidelity PCR system (Boehringer Mannheim) according to the instructions of the manufacturer.

The amplified DNA fragment containing the fungal signal sequence fused to the *E. chrysanthemi* PME gene was cloned into the PCR 2.1-TOPO cloning vector (Invitrogen) according to the instructions of the manufacturer. The cloned DNA fragment was sequenced using a Thermo Sequenase fluorescent cycle sequencing kit (Amersham) and an ALF DNA sequencer (Pharmacia) following the recommendations of the manufacturer.

An EcoRI DNA fragment containing the fungal signal sequence and the *E. chrysanthemi* PME gene was excised from the PCR 2.1-TOPO cloning vector, and introduced into the fungal expression vector pPR42 (See WO 9838321 A) containing the XlnB promoter and the TrpC terminator generating the vector pPR42-FS-PMEA (FIG. 4).

Transformation of *Aspergillus niger*.

The pPR42-FS-PMEA vector was transformed into an uridine auxotrophic mutant of *Aspergillus niger* using a protocol adapted from Van Someren et al (1991) Curr. Genet. 20, 293–299, using cotransformation with a *A. niger* orotidine-5'-phosphate-decarboxylase gene and selection for complementation of the uridine auxotrophic mutation (Goosen et al (1987) Curr. Genet. 11, 499–503).

For the purification of *Aspergillus niger* protoplasts spores from a PDA (Potato Dextrose Agar-Difco Lab. Detroit) plate, containing 5 mM uridine, incubated for 3–4 days at 30° C. are washed off in 10 ml ST (8 g/l NaCl, 0.5 g/l Tween 20). One million spores pr ml are inoculated in 200 ml growth medium in a 500 ml shaking flask.

The growth medium contains: 6 g/l $NaNO_3$, 1.5 g/l $KH_2PO_4$, 0.5 g/l $MgSO_4$, $7H_2O$, 0.5 g/l KCL, 10 mM $(NH_4)_2SO_4$, 0.2% Casing enzymatic hydrolysate (Sigma C-0626), 2% glucose, 0.5% Yeast extract (Difco 0127-17-9), 10 mM Uridine, 10 mg/l EDTA, 4.4 mg/l $ZnSO_4$, $7H_2O$, 1 mg/l $MnCl_2$, $4H_2O$, 0.32 mg/l $CoCl_2$, $6H_2O$, 0.32 mg/l $CuSO_4$, $5H_2O$, 0.22 mg/l $(NH_4)_6Mo_7O_{24}$, $4H_2O$, 1.47 mg/l $CaCl_2$, $2H_2O$, 1.0 mg/l $FeSO_4$, $7H_2O$, pH 6.0.

The flask is shaken at 230–250 rpm for 16–18 hours at 30° C. The mycelium is harvested using Miracloth and washed 2–3 times with SMC (1.33 M Sorbitol, 50 mM $CaCl_2$, 20 mM MES, pH 5.8). 1 g wet mycelium is resuspended in 20 ml of SMC containing 150 mg Lyzing enzyme (Sigma L-2265), in a sterile flask and incubated at 37° C., 80–100 rpm for 1–3 hours until protoplasts are released. The protoplasts are harvested by passing the suspension through 5 ml sterile glasswool followed by centrifugation at 3000 rpm for 10 min. The protoplasts are washed twice with 5–10 ml of STC (1.33 M Sorbitol, 50 mM $CaCl_2$, 10 mM Tris/HCl, pH 7.5) and finally resuspended in STC at $1 \times 10^8$ protoplasts/ml.

For the transformation, 0.2 ml of protoplasts are carefully mixed with 5–10 mg DNA (pPr42-FS-PMEA), 0.5 mg Selection DNA (pGW635—containing the orotidine-5'-phosphate-decarboxylase gene(Goosen et al (1987) Curr. Genet. 11, 499–503)) and 50 ml PEG solution (0.25 g/ml PEG 6000, 50 mM $CaCl_2$, 10 mM Tris/HCl, pH 7.5). The mixture is incubated for 20 min. at room temperature after which 2 ml of PEG solution is carefully added and mixed. After further incubation for 5 min at room temperature 6 ml of STC is added, and the mixture is carefully shaken. The mixture is centrifuged at 300 rpm for 10 min, and most of the supernatant is removed.

The protoplasts are resuspended in the remaining 1–2 ml of supernatant, mixed with TR soft agar (6 g/l $NaNO_3$, 1.5 g/l $KH_2PO_4$, 0.5 g/l $MgSO_4$, $7H_2O$, 0.5 g/l KCL, 1.22 M Sorbitol, 10 mg/l EDTA, 4.4 mg/l $ZnSO_4$, $7H_2O$, 1 mg/l $MnCl_2$, $4H_2O$, 0.32 mg/l $CoCl_2$, $6H_2O$, 0.32 mg/l $CuSO_4$, $5H_2O$, 0.22 mg/l $(NH_4)_6Mo_7O_{24}$, $4H_2O$, 1.47 mg/l $CaCl_2$, $2H_2O$, 1.0 mg/l $FeSO_4$, $7H_2O$, 0.8% agar (Difco 0140-01), pH 6.0, and plated on TR plates (As TR soft agar but with 1.2% agar). Transformed colonies are picked and replicated on fresh TR plates.

Growth of *A. niger* Transformants for Expression of the *E. chrysanthemi* PME Gene.

For the expression of the *E. chrysanthemi* PME gene in *A. niger* transformants, spores (aprox 500,000 pr ml) are inoculated in induction medium (6 g/l $NaNO_3$, 1.5 g/l $KH_2PO_4$, 0.5 g/l $MgSO_4$, $7H_2O$, 0.5 g/l KCL, 10 mM $(NH_4)_2SO_4$, 10 mg/l EDTA, 4.4 mg/l $ZnSO_4$, $7H_2O$, 1 mg/l $MnCl_2$, $4H_2O$, 0.32 mg/l $CoCl_2$, $6H_2O$, 0.32 mg/l $CuSO_4$, $5H_2O$, 0.22 mg/l $(NH_4)_6Mo_7O_{24}$, $4H_2O$, 1.47 mg/l $CaCl_2$, $2H_2O$, 1.0 mg/l $FeSO_4$, $7H_2O$, 29.4 g/l $Na_3citrate, 2H_2O$, 0.2% Casein enzymatic hydrolysate (Sigma C-0626) and 2% Xylose) and incubated at 30° C. with shaking. After 2–3 days samples of the supernatant are taken daily and analysed for PME activity.

STUDY EXPERIMENT 3

The PME expressed in *Aspergillus niger* was tested for activity by the method described earlier. The specific activity was 600 U/mg protein.

Characterisation of the protein by SDS-PAGE revealed a protein with MW of 36 kDa. The protein was not glycosylated as indicated by the correct MW of the mature protein. MALDI TOF MS analysis of the recombinant PME protein also showed that the enzyme was not glycosylated. From the amino acid sequence two potential N-glycosylation sites were detected.

The protein was N-terminal sequenced and the N-terminal sequence was: A T T Y N A V V. This result shows that both the fungal signal peptide and the signal peptide from Erwinia are processed correctly and the mature protein is produced without any N-terminal signal peptides.

The pH optimum of the *E. chrysanthemi* expressed in *A. niger* is pH 5.5 to 7. The same pH profile was also seen for the *E. chrysanthemi* PME expressed in *E. coli*.

The Aspergillus expressed *E. chrysanthemi* PME was concentrated by ultrafiltration using YM 10 membrane (Amicon) prior to enzymatic modification of pectin.

Modification of Pectin with Aspergillus Expressed PME Obtainable from *Erwinia chrysanthemi*

Methods:

Enzymatic treatment of pectin with PME from *E. chrysanthemi*.

40 g GRINDSTED™ Pectin URS 1400 was dissolved in hot water under efficient stirring. 7.8 g NaCl was added and the volume adjusted to 1.33 l with water. The pectin solution was stirred until all material had dissolved and then cooled to 37° C. pH was increased to 5.5, using 1 N NaOH and efficient stirring. 26 U of PME was added and pH and temperature was kept constant at 5.5 and 37° C. by automatic dosage of 1N NaOH during about two hours, until 8 ml 1 N NaOH was consumed. pH of the solution was lowered to 3.0 by addition of 2 N HCl to stop the enzymatic reaction. The pectin solution was then heated to 70° C. for 5 min to completely inactivate the enzyme. The treated pectin was precipitated with one volume isopropyl alcohol, washed with 60 vol. % isopropyl alcohol and pressed to 50% dry matter. The treated pectin was then air dried at 50° C. and finally milled to a dry powder. 38.7 g enzyme treated pectin was isolated.

Results:

The pectin treated with PME from *E. chrysanthemi* which was expressed in Aspergillus was analysed with respect to % DE and calcium sensitivity (CS). The results showed that the enzymatic treated pectin has increased calcium sensitivity compared to the mother pectin. The enzymatic treatment results in a HE-pectin with significant higher calcium sensitivity. These are the same results which were obtained with the *E. chrysanthemi* PME expressed in *E. coli*.

|  | % DE | CS |
|---|---|---|
| GRINDSTED ™ Pectin URS 1400 | 82.1% | 1.11 |
| Enzymatic treated sample | 75.3% | 2.01 |

Discussion

The bacterial PME (*Erwinia chrysanthemi*) has been isolated and characterized. URS pectin with DE 81% has been de-esterified with this PME to modified pectins with varying DE%. The characterization of the pectin revealed that the pectin is a moderately Ca-sensitive pectin or a very Ca-sensitive pectin at a high DE%. We believe that this is the first time that a bacterial PME has been shown to de-methylate pectin in a block-wise manner.

With the specific embodiment of the present invention, the modified pectin with DE of 78% has been tested in a acidified milk drink system. The results showed that the modified pectin stabilises the protein in the acidified milk drink at a concentration of 0.15% pectin. The URS pectin do only stabilise the proteins in the acidified milk drink test at a very high concentration of pectin (>0.5).

Likewise, we believe that this is the first time it has been shown that a bacterial PME can de-methylate pectin in a blockwise manner and, in addition, produce a Ca-sensitive pectin and, in addition, wherein the modified pectin can stabilise acidified milk drink.

PROTOCOLS

PROTOCOL I

CALCIUM SENSITIVITY INDEX (CS)

Calcium sensitivity is measured as the viscosity of a pectin dissolved in a solution with 57.6 mg calcium/g pectin divided by the viscosity of exactly the same amount of pectin in solution, but without added calcium. A calcium insensitive pectin has a CS value of 1.

4.2 g pectin sample is dissolved in 550 ml hot water with efficient stirring. The solution is cooled to about 20° C. and the pH adjusted to 1.5 with 1N HCl. The pectin solution is adjusted to 700 ml with water and stirred. 145 g of this solution is measured individually into 4 viscosity glasses. 10 ml water is added to two of the glasses (double determinations) and 10 ml of a 250 mM $CaCl_2$ solution is added to the other two glasses under stirring.

50 ml of an acetate buffer (0.5 M, pH about 4.6) is added to all four viscosity glasses under efficient magnetic stirring, thereby bringing the pH of the pectin solution up over pH 4.0. The magnets are removed and the glasses left overnight at 20° C. The viscosities are measured the next day with a Brookfield viscometer. The calcium sensitivity index is calculated as follows:

$$CS = \frac{\text{Viscosity of a solution with 57.6 mg } Ca^{2+}/g \text{ pectin}}{\text{Viscosity of a solution with 0.0 mg } Ca^{2+}/g \text{ pectin}}$$

PROTOCOL II

DEGREE OF ESTERIFICATION (%DE)

To 50 ml of a 60% isopropanol and a 5% HCl solution is added 2.5 g pectin sample and stirred for 10 min. The pectin solution is filtered through a glass filter and washed with 15 ml 60% isopropanol/5% HCl solution 6 times followed by further washes with 60% isopropanol until the filtrate is free of chlorides. The filtrate is dried overnight at 80° C.

20.0 ml 0.5 N NaOH and 20.0 ml 0.5 N HCl is combined in a conical flask and 2 drops of phenolphtalein is added. This is titrated with 0.1 N NaOH until a permanent colour change is obtained. The 0.5 N HCl should be slightly stronger than the 0.5N NaOH. The added volume of 0.1 N NaOH is noted as $V_0$.

0.5 g of the dried pectin sample (the filtrate) is measured into a conical flask and the sample is moistened with 96% ethanol. 100 ml of recently boiled and cooled destilled water is added and the resulting solution stirred until the pectin is completely dissolved. Then 5 drops of phenolphtalein are added and the solution titrated with 0.1 N NaOH (until a change in colour and pH is 8.5). The amount of 0.1 N NaOH used here is noted as $V_1$. 20.0 ml of 0.5 N NaOH is added and the flask shaken vigously, and then allowed to stand for 15 min. 20.0 ml of 0.5 N HCl is added and the flask is shaken until the pink colour disappears. 3 drops of phenolphtalein are then added and then the resultant solution is titrated with 0.1 N NaOH. The volume 0.1 N NaOH used is noted as $V_2$.

The degree of esterification (% DE: % of total carboxy groups) is calculated as follows:

$$\% DE = \frac{V_2 - V_0}{V_1 + (V_2 - V_0)}$$

PROTOCOL III

DRINK TEST

1. Introduction

The following describes a protocol that only uses about 1.7 g pectin to as little as possible. The methods used to evaluate the performance of the system are viscometry, centrifugal sedimentation, and particle size determination.

2. Materials and Methods 2.1 Materials

Skim milk powder with approx. 36% protein was obtained from Mejeriernes Fælles Indkøb (Kolding, Denmark). Pectins for testing were obtained by treatment of a pectin with a modified PME according to the present invention. These pectins may have different properties such as degree of esterification and molecular weight, depending on the type of modified PME used.

2.2 Preparation of Milk Drink

The milk drinks were made by mixing an acidified milk solution and a pectin solution. followed by further processing.

A milk solution was made by dissolving 17% (w/w) skimmilk powder in distilled water at 68° C. and stirring for 30 min. The milk solution was then acidified to pH 4.1 at 30° C. by addition of 3% (w/w) glucono-d-lactone (GDL).

The pectin solution was made up in several steps. First pectin was dry mixed with dextrose at a 3:2 weight ratio, and then a 1.11% (w/w) solution of this mixture in distilled water was made. The last step in the preparation of the pectin solution was to add sucrose to an end concentration of 17.8% (w/w).

Milk drinks were then prepared by mixing 1 part of milk solution with 1.13 parts (w/w) of pectin solution, followed by heat treatment (see section 3.2) and homogenisation at 20–22 MPa and 20° C. using a Mini Jet Homogeniser (Burgaud et. al. 1990). By following this procedure, the final concentration of pectin in the milk drink was 0.3% (w/w). All samples were produced in duplicate stored at 5° C. and tested for viscosity, particle size and sedimentation the following day.

2.3 Viscosity Measurement

The viscosity was measured using a Bohlin VOR Rheometer system (Bohlin Instruments, Metric Group Ltd., Gloucestershire, Great Britain). Thermostatation was achieved by a Bohlin lower-plate temperature control unit. The viscosity was measured at a shear rate of $91.9\ s^{-1}$. The measuring temperature was 20° C., and the samples were held at 20° C. for approximately 1 hour before measurement. The measuring system used was C 14 (a coaxial cylindrical system). The torque element used was 0.25 g cm. Integration time was 5 s, measurement internal was 30 s, and no autozero was used. Instrumental control and primary data processing were done on a PC with the Bohlin Rheometer Software version 4.05.

2.4 Particle Size Measurement

The particle mean diameter, D[4.3], was measured with a Malvern Mastersizer Micro Plus (Malvern Instruments Limited, Worcestershire, UK). Instrumental settings were: presentation code: 5NBD, and Analysis Model: polydisperse. Instrumental control and primary data processing were done on a PC with Mastersizer Microplus for Windows, version 2.15.

Ultrafiltration permeate obtained from a batch of acidified milk drink made with pectin no. 4 was used for dilution. Ultrafiltration was done using a DDS UF Lab 20-0.36 module fitted with GR61PP membranes, having a molecular weight cut-off of 20.000 Da.

2.5 Sedimentation

Sedimentation measurements were performed by centrifugation of the samples using an IEC Centra-8R Centrifuge (International Equipment, Needham Hts, Mass. USA). 2.5 g acidified milk drink was centrifuged for 25 min at 20° C. and 2400 g. The supernatant was removed, the tubes were left up side down for 15 min, and the weight of the sediment was determined and expressed as a percentage (of the amount of milk drink used). Duplicate measurements were made of each sample.

3. Results and Discussion 3.1 Size of Test System

This new system is small compared to the previous test systems but it still maintains the same properties as the existing test system based on 550 g acidified milk drink. The easiest way to make a model system for testing pectins in acidified milk drinks would be to simply mix stirred acidified milk drink with a pectin solution, and make the measurements on this mixture. This also has the advantage that it can be done virtually at any scale. However, Glahn and Rolin showed that a homogenisation reduces the amount of pectin needed for stabilisation and that both homogenisation and heat treatment have very considerable effects on stability. Since both homogenisation and heat treatment were included in the existing system at 550 g scale, as they are in industrial processes, both treatments also needed to be present in the small scale system.

In industry both upstream (before heating) and downstream (after heating) homogenisation is used. In this model system we chose to put the homogenisation in after heat treatment because this gives a more homogeneous sample and thereby makes it easier to obtain reproducible measurements of e.g. viscosity.

To achieve a reproducible homogenisation with the Mini Jet Homogeniser, and to compensate for various losses during sample transfer, it was desirable to operate with 40 ml of sample at the homogenisation stage. Since only 8–9 ml was needed for the tests (2.5 ml for viscometry, 5 ml for sedimentation, and 0.5–1 ml for particle size determination), the step that required the largest amount of sample was the homogenisation, and the result was therefore that the existing test system was scaled down from 550 g to 40 g milk drink.

3.2 Heat Treatment

To make the scaled down system mimic the existing test system as closely as possible it was desirable to make modifications to the heat treatment step. With the existing 550 g system heating took place in a 600 ml Blue-cap bottle for 30 min in a 75° C. water bath, with stirring every 5 minutes.

With the new 40 g system the heat treatment was done in a 50 ml plastic centrifuge tube placed inside a 600 ml Blue-cap bottle filled with water. Here 75° C. in the water bath gave too strong a heating, probably because the thermal conductivity of water is larger than that of coagulated milk. Different temperatures between 70 and 75° C. were therefore tested, and it was found that 72° C. for 30 minutes, without stirring, gave a good approximation to the temperature profile in the large system.

3.3 Testing of Small Scale System

If a milk drink stabilised with a pectin treated with a modified PME according to the present invention showed little sedimentation and small particles, then that indicates a good pectin to use and moreover is indicative that the modified PME according to the present invention is suitable for such a use.

4. Conclusion

A system for testing the stabilising power of pectins in acidified milk drinks has successfully been scaled down from 550 g to 40 g milk drink, meaning that the required amount of pectin is reduced from ca. 1.7 g to ca. 0.15 g. This is small enough to allow screening of experimental pectin samples treated with modified pectins according to the present invention. A high correlation between results obtained for particle size, viscosity and sedimentation between the two methods has been demonstrated. The scaled down method is relatively simple, although it still contains both heating and homogenisation which is considered important for industrial relevance.

PROTOCOL IV

PME ACTIVITY

PME catalyses the cleavage of methylester groups from pectin. During the purification steps PME can be detected by a fast method using methyl red indicator test. Due to cleavage of methyl groups from galacturonic acid residues in the pectin chain, carboxyl groups are formed and the pH will then drop in the assay. The pH indicator—methyl red—changes colour at pH drop from yellow (pH 6.2) to pink (pH 4.2). Typically, the assay will contain 1 ml 0.5% Grindsted™ Pectin 1450 (DE 70%) (supplied by Danisco Ingredients, Danisco A/S) solubilized in 0.15 M NaCl pH 7 and 25 µl sample. The samples which then show positive methyl red test after 10 min incubation at 30° C. are then further measured by the titration method (Versteeg et al (1978) Lebensmittel.-Wiss. u. Technol., 11: 267–274).

With the titration method the assay will typically contain 10 ml 0.5% lime pectin (Grindsted™ Pectin 1450—supplied by Danisco Ingredients, Danisco A/S) solubilized in 0.15 M NaCl pH 6.8 and 10–100 µl sample. Titration is performed with 0.02 M NaOH and the reaction is measured at room temperature. An automatic titrator can be used (Versteeg et al. (1978) Lebensmittel.-Wiss. u. Technol., 11: 267–274).

For convenience we now present a Table indicating the codes used for the amino acids.

| AMINO ACID | THREE LETTER ABBREVIATION | ONE LETTER SYMBOL |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

REFERENCES

Glahn, P. E, Rolin, C.: Food Ingredients Europe, Conf. Proc. 252–256 (1994)

Burgaud, I., Dickinson, E., Nelson, E.: International Journal of Food Science and Technology 25. 39–46 (1990)

Finer J J, Vain P, Jones M W & McMullen M D (1992) Development of the particle inflow gun for DNA delivery to plant cells Plant cell Reports 11: 323–328

Klein T M, Wolf E D, Wu R & Sanford J C (1987) High-velocity microprojectiles for delivery nucleic acids into living cells Nature 327: 70–73

Sanford J C, Klein T M. Wolf E D & Allen N (1987) Delivery of substances into cells and tissues using a particle bombardment process Particulate Science and Technology 5: 27–37

Vain P, Keen N, Murillo J, Rathus C, Nemes C & Finer J J (1993) Development of the Particle Inflow Gun Plant cell, Tissue and Organ Culture 33: 237–246

Penninga D, van der Veen B A, Knegtel R M A, van Hijum S A F T, Rozeboom H J, Kalk K H, Dijkstra B W, Dijkhuizen L. (1996) The raw starch binding domain of cyclodextrin glycosyltransferase from *Bacillus circulans* strain 251. J. Biol. Chem. 271: 2777–32784.

What is claimed is:

1. A process for treating a pectin with pectin methyl esterase (PME) to produce a PME-treated high ester pectin, comprising the step of contacting a pectin with an Erwinia PME, having a pH optimum with lime pectin of about pH 7.0, that is capable of block-wise de-esterification of the pectin, to produce a PME-treated high ester pectin that contains from about 70% to about 80% ester groups.

2. The process according to claim 1 wherein the PME has a molecular weight of about 36,000 D and/or a pI of about>9 and/or a temperature optimum with lime pectin of about 48° C.

3. The process according to claim 1 wherein the pME comprises the amino acid sequence shown as SEQ.I.D. No.2, or an amino acid sequence having PME activity with at least 75% homology to SEQ ID No:2.

4. The process according to claim 1 wherein the PME has the amino acid sequence shown as SEQ.I.D. No.2, or an amino acid sequence having PME activity with at least 75% homology to SEQ ID No:2.

5. The process according to claim 1 wherein the PME has the amino acid sequence shown as SEQ.I.D. No.2.

6. The process according to claim 1 wherein the PME has been expressed by a nucleotide sequence comprising the nucleotide sequence shown as SEQ.I.D. No.1, or a nucleotide sequence with at least 75% homology to SEQ ID No:1, or combinations thereof.

7. The process according to claim 1 wherein the PME has been expressed by a nucleotide sequence having the nucleotide sequence shown as SEQ.I.D. No.1, or a nucleotide sequence with at least 75% homology to SEQ ID No:1.

8. The process according to claim 1 wherein the PME has been expressed by a nucleotide sequence having the nucleotide sequence shown as SEQ.I.D. No.1.

9. The process according to claim 1 wherein the PME has been prepared by use of known recombinant DNA techniques.

10. The process according to claim 1 wherein the pectin is in contact with the PME in the presence of sodium ions.

11. The process according to claim 10 wherein the sodium ions are derived from NaCl, $NaNO_3$, or $Na_2SO_4$ or combinations thereof.

12. The process according to claim 1 wherein the process includes the further step of isolating the PME-treated pectin from remaining active PME.

13. The process according to claim 12 wherein the PME treated pectin contains from about 72% to about 80% ester groups.

14. The process according to claim 12 wherein the PME treated pectin contains from about 74% to about 80% ester groups.

15. The process according to claim 12 wherein the PME treated pectin contains from about 76% to about 80% ester groups.

16. The process according to claim 12 wherein the PME treated pectin contains from about 77% to about 80% ester groups.

17. The process according to claim 1 wherein the process includes the further step of adding the PME-treated pectin to a medium that is suitable for human or animal consumption.

18. The process according to claim 17 wherein the medium is an aqueous solution.

19. The process according to claim 18 wherein the aqueous solution is a beverage.

20. The process according to claim 17 wherein the medium is an acidic environment.

21. The process according to claim 20, wherein the acidic environment has a pH of from about 3.5 to about 5.5.

22. The process according to claim 21 wherein the acidic environment has a pH of about 4.

23. The process according to claim 19, wherein the beverage is a acidified milk drink.

24. The process according to claim 17 herein the medium of comprises a protein.

25. The process according to claim 22 wherein the protein is derived from or is obtainable from or is in a dairy product.

26. The process according to claim 22 wherein the protein is derived from or is obtainable from or is in a plant product.

27. The process according to claim 20, wherein the acidic environment has a pH of from 4 to about 5.5.

28. A method for reducing the number of ester groups in a pectin in a block-wise manner, comprising the step of contacting a pectin with a pectin methyl esterase (PME) to produce a PME-treated pectin that contains about 70% to about 80% ester groups and which PME comprises the amino acid sequence shown as SEQ.I.D. No.2 or an amino acid sequence with at least 75% homology to SEQ ID No:2, wherein said PME is not a plant PME and is capable of block-wise de-esterification of the pectin.

29. A method for de-esterifying two or more adjacent galacturonic acid residues of a pectin on a pectin chain, comprising the step of contacting a pectin with a pectin methyl esterase (PME) to produce a PME-treated pectin that contains about 70% to about 80% ester groups and which PME comprises the amino acid sequence shown as SEQ.I.D. No.2 or an amino acid sequence with at least 75% homology to SEQ ID No:2, wherein said PME is not a plant PME and is capable of block-wise de-esterification of the pectin.

30. The process according to claim 28 or 29 wherein the PME is obtained from a micro-organism.

31. The process according to claim 30 wherein the PME is obtained from a bacterium.

32. The process according to claim 17, wherein the medium is enriched with a protein.

33. The process according to claim 32 wherein the protein is derived from or is obtainable from or is in a dairy product.

34. The process according to claim 32 wherein the protein is derived from or is obtainable from or is in a plant product.

* * * * *

SEQUENCE LISTING

<160> NUMBER OF SEQ ID NOS: 21

<210> SEQ ID NO 1
<211> LENGTH: 1101
<212> TYPE: DNA
<213> ORGANISM: Erwinia chrysanthemi

<400> SEQUENCE: 1

```
atgttaaaaa cgatctctgg aaccctcgcg ctgtcgctga ttatcgctgc cagcgtacat      60
caggcacagg cagcgaccac ctacaacgct gtggtatcaa aatcctccag cgacggcaaa     120
acaatcaaaa ctattgccga cgcaattgcc agcgcccag caggcagcac gccgttcgtc     180
attttgatca agaacggcgt ctataatgaa cgcctgacga ttacccgcaa taacctgcat     240
ctgaaaggcg aaagtcgtaa cggtgcggtc attgcggctg ccacggcggc gggcaccctg     300
aaatcggacg gcagcaagtg gggaacggca ggcagcagca ccatcaccat cagcgccaag     360
gatttcagcg cccagtcgct gaccattcgc aacgactttg atttcccggc caatcaggcc     420
```

-continued

```
aaaagcgaca gcgacagcag taaaatcaag gacacgcagg cagttgcgct ctatgtcacc    480
aaaagcggcg accgcgccta cttcaaagac gtcagtctgg tcggctatca ggacacgctg    540
tatgtttccg gcggccgcag tttcttctcc gactgccgta tcagcggcac ggttgacttt    600
atctttggcg acggcaccgc gctgttcaac aactgcgatc tggtttcccg ctatcgcgct    660
gatgtgaaaa gcggcaatgt tccggctac  ctgaccgcgc cagcaccaa  catcaatcag    720 aagtatggcc tggtgatcac caacagtcgc gtgatacggg aaagtgactc tgtaccggcg    780
aaaagctacg gctgggtcg  ccctggcat  ccaacaacaa cctgctctga tggccgttac    840
gcgaatccga acgctattgg tcagaccgtt ttcctgaaca ccagcatgga taatcatatt    900
tatggttggg acaagatgtc cggcaaggac aaaaacggca acaccatctg gttcaacccg    960
gaagattccc gtttcttcga gtacaaatcc tatggcgcgg gagcggcggt gagcaaagac   1020
cgccgacagt tgactgacgc acaggcggca gagtacacgc agagcaaagt cctgggcgac   1080
tggacgccga cattaccctg a                                             1101
```

<210> SEQ ID NO 2
<211> LENGTH: 366
<212> TYPE: PRT
<213> ORGANISM: Erwinia chrysanthemi

<400> SEQUENCE: 2

```
Met Leu Lys Thr Ile Ser Gly Thr Leu Ala Leu Ser Leu Ile Ile Ala
  1               5                  10                  15

Ala Ser Val His Gln Ala Gln Ala Ala Thr Thr Tyr Asn Ala Val Val
             20                  25                  30

Ser Lys Ser Ser Ser Asp Gly Lys Thr Ile Lys Thr Ile Ala Asp Ala
         35                  40                  45

Ile Ala Ser Ala Pro Ala Gly Ser Thr Pro Phe Val Ile Leu Ile Lys
     50                  55                  60

Asn Gly Val Tyr Asn Glu Arg Leu Thr Ile Thr Arg Asn Asn Leu His
 65                  70                  75                  80

Leu Lys Gly Glu Ser Arg Asn Gly Ala Val Ile Ala Ala Thr Ala
             85                  90                  95

Ala Gly Thr Leu Lys Ser Asp Gly Ser Lys Trp Gly Thr Ala Gly Ser
            100                 105                 110

Ser Thr Ile Thr Ile Ser Ala Lys Asp Phe Ser Ala Gln Ser Leu Thr
        115                 120                 125

Ile Arg Asn Asp Phe Asp Phe Pro Ala Asn Gln Ala Lys Ser Asp Ser
    130                 135                 140

Asp Ser Ser Lys Ile Lys Asp Thr Gln Ala Val Ala Leu Tyr Val Thr
145                 150                 155                 160

Lys Ser Gly Asp Arg Ala Tyr Phe Lys Asp Val Ser Leu Val Gly Tyr
                165                 170                 175

Gln Asp Thr Leu Tyr Val Ser Gly Gly Arg Ser Phe Phe Ser Asp Cys
            180                 185                 190

Arg Ile Ser Gly Thr Val Asp Phe Ile Phe Gly Asp Gly Thr Ala Leu
        195                 200                 205

Phe Asn Asn Cys Asp Leu Val Ser Arg Tyr Arg Ala Asp Val Lys Ser
    210                 215                 220

Gly Asn Val Ser Gly Tyr Leu Thr Ala Pro Ser Thr Asn Ile Asn Gln
225                 230                 235                 240

Lys Tyr Gly Leu Val Ile Thr Asn Ser Arg Val Ile Arg Glu Ser Asp
                245                 250                 255
```

-continued

```
Ser Val Pro Ala Lys Ser Tyr Gly Leu Gly Arg Pro Trp His Pro Thr
            260                 265                 270

Thr Thr Phe Ser Asp Gly Arg Tyr Ala Asn Pro Asn Ala Ile Gly Gln
        275                 280                 285

Thr Val Phe Leu Asn Thr Ser Met Asp Asn His Ile Tyr Gly Trp Asp
    290                 295                 300

Lys Met Ser Gly Lys Asp Lys Asn Gly Asn Thr Ile Trp Phe Asn Pro
305                 310                 315                 320

Glu Asp Ser Arg Phe Phe Glu Tyr Lys Ser Tyr Gly Ala Gly Ala Ala
                325                 330                 335

Val Ser Lys Asp Arg Arg Gln Leu Thr Asp Ala Gln Ala Ala Glu Tyr
            340                 345                 350

Thr Gln Ser Lys Val Leu Gly Asp Trp Thr Pro Thr Leu Pro
        355                 360                 365

<210> SEQ ID NO 3
<211> LENGTH: 22
<212> TYPE: PRT
<213> ORGANISM: Artificial Sequence
<220> FEATURE:
<221> NAME/KEY: SITE
<222> LOCATION: (1)
<223> OTHER INFORMATION: Preferably Xaa is Ala, Val, Gly or Thr
<221> NAME/KEY: SITE
<222> LOCATION: (2)
<223> OTHER INFORMATION: Preferably Xaa is Val or Leu
<221> NAME/KEY: SITE
<222> LOCATION: (3)
<223> OTHER INFORMATION: Preferably Xaa is Leu, Phe or Ile
<221> NAME/KEY: SITE
<222> LOCATION: (5)
<223> OTHER INFORMATION: Preferably Xaa is Asn, Asp, Lys, Gly or Ser
<221> NAME/KEY: SITE
<222> LOCATION: (6)
<223> OTHER INFORMATION: Preferably Xaa is Cys or Ser
<221> NAME/KEY: SITE
<222> LOCATION: (7)
<223> OTHER INFORMATION: Preferably Xaa is Asp, Gln, Lys, Glu, Tyr or
      Leu
<221> NAME/KEY: SITE
<222> LOCATION: (8)
<223> OTHER INFORMATION: Preferably Xaa is Ile, Leu or Phe
<221> NAME/KEY: SITE
<222> LOCATION: (9)
<223> OTHER INFORMATION: Preferably Xaa is His, Asn, Val, Met or Leu
<221> NAME/KEY: SITE
<222> LOCATION: (10)
<223> OTHER INFORMATION: Preferably Xaa is Ala, Cys, Ile, Pro, Leu,
      Cys or Ser
<221> NAME/KEY: SITE
<222> LOCATION: (12)
<223> OTHER INFORMATION: Preferably Xaa is Lys, Arg, Leu, Gln or Tyr
<221> NAME/KEY: SITE
<222> LOCATION: (13)
<223> OTHER INFORMATION: Preferably Xaa is Pro, Gly or Arg
<221> NAME/KEY: SITE
<222> LOCATION: (14)
<223> OTHER INFORMATION: Preferably Xaa is Asn, Gly, Met, Ala, Leu,
      Arg or Ser
<221> NAME/KEY: SITE
<222> LOCATION: (15)
<223> OTHER INFORMATION: Preferably Xaa is Ser, Lys, Glu, Pro or Asp
<221> NAME/KEY: SITE
<222> LOCATION: (16)
<223> OTHER INFORMATION: Preferably Xaa is Gly, Tyr, His, Asn,
      Lys or Val
<221> NAME/KEY: SITE
<222> LOCATION: (17)
<223> OTHER INFORMATION: Preferably Xaa is Gln, Gly or Lys
<221> NAME/KEY: SITE
<222> LOCATION: (18)
```

```
<223> OTHER INFORMATION: Preferably Xaa is Lys, Gln, Phe, Tyr or Ser
<221> NAME/KEY: SITE
<222> LOCATION: (19)
<223> OTHER INFORMATION: Preferably Xaa is Asn, Cys or Gly
<221> NAME/KEY: SITE
<222> LOCATION: (20)
<223> OTHER INFORMATION: Preferably Xaa is Met, Leu, Ile, Thr, Val,
      His or Asn
<221> NAME/KEY: SITE
<222> LOCATION: (21)
<223> OTHER INFORMATION: Preferably Xaa is Val or Ile
<221> NAME/KEY: SITE
<222> LOCATION: (22)
<223> OTHER INFORMATION: Preferably Xaa is Thr, Leu or Ser
<223> OTHER INFORMATION: Description of Artificial Sequence: Formula (I)

<400> SEQUENCE: 3

Xaa Xaa Xaa Gln Xaa Xaa Xaa Xaa Xaa Xaa Arg Xaa Xaa Xaa Xaa Xaa
  1               5                  10                  15

Xaa Xaa Xaa Xaa Xaa Xaa
             20

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 4
agtcgacgtg tatgttaaaa acgatctctg g                              31

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 5
agcggccgca attcgtcagg gtaatgtcgg                                30

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 6
gtaaacgacg gccagt                                               16

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 7
ggaaacagct atgaccatg                                            19

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Primer
```

<400> SEQUENCE: 8
gattatccat gctggtg                                            17

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
cggcgtctat aatgaacg                                           18

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 10
gcgacagcga cagcag                                             16

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 11
ccgtggcagc cgcaatgac                                          19

<210> SEQ ID NO 12
<211> LENGTH: 56
<212> TYPE: DNA
<213> ORGANISM: Artificial Sequence
<220> FEATURE:
<223> OTHER INFORMATION: Description of Artificial Sequence: pSPORT1
      EcoR1 - HindIII fragment

<400> SEQUENCE: 12
aagcttggat cctctagagc ggccgccgac tagtgagctc gtcgacccgg gaattc    56

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 13
cacacagaat tcattaaaga ggagaaatta acccgtcgac ccgggag            47

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 14
ctcccgggtc gacgggttaa tttctcctct ttaatgaatt ctgtgtg            47

-continued

<210> SEQ ID NO 15
<211> LENGTH: 51
<212> TYPE: DNA
<213> ORGANISM: Aspergillus niger

<400> SEQUENCE: 15
atggttaagt caattcttgc atccgttctc tttgcggcga ctgcgctggc c        51

<210> SEQ ID NO 16
<211> LENGTH: 17
<212> TYPE: PRT
<213> ORGANISM: Aspergillus niger

<400> SEQUENCE: 16

Met Val Lys Ser Ile Leu Ala Ser Val Leu Phe Ala Ala Thr Ala Leu
 1               5                  10                  15

Ala

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 17
gcggcgactg cgctggccat gttaaaaacg atctctggaa ccc                  43

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 18
aagtcaattc ttgcatccgt tctctttgcg gcgactgcgc                      40

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 19
tgaattctca tggttaagtc aattcttgca tccg                            34

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 20
tactagtgtc agggtaatgt cggc                                       24

<210> SEQ ID NO 21
<211> LENGTH: 8

```
-continued

<212> TYPE: PRT
<213> ORGANISM: Erwinia chrysanthemi

<400> SEQUENCE: 21

Ala Thr Thr Tyr Asn Ala Val Val
 1               5
```